US 12,196,676 B2

(12) United States Patent
Mangeat et al.

(10) Patent No.: US 12,196,676 B2
(45) Date of Patent: Jan. 14, 2025

(54) OPTICAL PROBE COMPRISING A WAVEGUIDE AND METHOD FOR REAL-TIME AND IN-SITU MEASUREMENTS OF SOIL PROPERTIES

(71) Applicant: CHRYSALABS INC., Montreal (CA)

(72) Inventors: Gabriel Mangeat, Montreal (CA); Benjamin De Leener, Montreal (CA); Jacques Michiels, Montreal (CA)

(73) Assignee: CHRYSALABS INC. (CA)

( * ) Notice: Subject to any disclaimer, the term of this patent is extended or adjusted under 35 U.S.C. 154(b) by 161 days.

(21) Appl. No.: 17/802,066

(22) PCT Filed: Feb. 25, 2021

(86) PCT No.: PCT/CA2021/050233
§ 371 (c)(1),
(2) Date: Aug. 24, 2022

(87) PCT Pub. No.: WO2021/168574
PCT Pub. Date: Sep. 2, 2021

(65) Prior Publication Data
US 2023/0026607 A1    Jan. 26, 2023

Related U.S. Application Data

(60) Provisional application No. 62/981,729, filed on Feb. 26, 2020.

(51) Int. Cl.
*G01N 21/01* (2006.01)
*G01N 21/17* (2006.01)
(Continued)

(52) U.S. Cl.
CPC ......... *G01N 21/62* (2013.01); *G01N 21/314* (2013.01); *G01N 21/3554* (2013.01);
(Continued)

(58) Field of Classification Search
CPC ............... G01N 21/17; G01N 21/31; G01N 2021/3125; G01N 2021/3129;
(Continued)

(56) References Cited

U.S. PATENT DOCUMENTS

| 4,994,671 | A | 2/1991 | Safinya et al. |
| 5,128,882 | A | 7/1992 | Cooper et al. |

(Continued)

FOREIGN PATENT DOCUMENTS

| CA | 2530707 A1 | 1/2005 |
| CN | 104483285 A | 4/2015 |

(Continued)

OTHER PUBLICATIONS

Ben-Dor, Eyal, Daniela Heller, and Alexandra Chudnovsky, "A Novel Method of Classifying Soil Profiles in the Field using Optical Means," Soil Science Society of America Journal 72.4 (2008): 1113-1123 (Year: 2008), 11 pages.

(Continued)

*Primary Examiner* — Allen C. Ho
(74) *Attorney, Agent, or Firm* — Amundsen Davis, LLC

(57) ABSTRACT

There are provided an optical probe and method for analysing a soil located in an underground area. The optical probe includes a probe head insertable into the underground area to contact the soil, the probe head including a waveguide having opposite first and second ends both optically shielded from the soil; a light source configured to generate a multiwavelength interrogating beam and optically coupled to the first end of the waveguide so that the multiwavelength interrogation beam is inputted in the waveguide to propagate towards the second end; and a detector optically coupled to the second end of the waveguide to detect said multiwavelength interrogation beam. The waveguide includes an unshielded interaction zone extending between the first and (Continued)

second ends providing a wavelength-dependent attenuation of the multiwavelength interrogation beam through interaction with the soil.

20 Claims, 17 Drawing Sheets

(51) Int. Cl.
*G01N 21/31* (2006.01)
*G01N 21/33* (2006.01)
*G01N 21/35* (2014.01)
*G01N 21/3554* (2014.01)
*G01N 21/552* (2014.01)
*G01N 21/62* (2006.01)
*G01N 21/63* (2006.01)
*G01N 21/85* (2006.01)
*G01N 33/24* (2006.01)

(52) U.S. Cl.
CPC ........... *G01N 21/552* (2013.01); *G01N 21/63* (2013.01); *G01N 21/8507* (2013.01); *G01N 33/24* (2013.01); *G01N 2021/3133* (2013.01); *G01N 2021/3181* (2013.01); *G01N 2021/855* (2013.01); *G01N 33/245* (2024.05); *G01N 2201/0627* (2013.01); *G01N 2201/0634* (2013.01); *G01N 2201/0636* (2013.01)

(58) Field of Classification Search
CPC ........ G01N 2021/3133; G01N 21/552; G01N 21/62; G01N 21/63; G01N 2021/855; G01N 21/01; G01N 2021/0106; G01N 2021/0112; G01N 2021/1734; G01N 2021/1736; G01N 2021/1738; G01N 2021/174; G01N 2021/3137; G01N 21/314; G01N 21/3151; G01N 2021/3155; G01N 21/33; G01N 21/35; G01N 21/3554; G01N 21/64; G01N 21/85
USPC ............. 250/253, 261, 269.1, 338.4, 339.01, 250/339.05, 339.1, 372
See application file for complete search history.

(56) References Cited

U.S. PATENT DOCUMENTS

| | | | |
|---|---|---|---|
| 5,491,344 A | 2/1996 | Kenny et al. | |
| 5,548,115 A * | 8/1996 | Ballard ................ | G01N 33/241 250/301 |
| 5,726,349 A | 3/1998 | Palmertree et al. | |
| 5,739,536 A | 4/1998 | Bucholtz et al. | |
| 5,902,939 A | 5/1999 | Ballard et al. | |
| 6,393,927 B1 | 5/2002 | Biggs et al. | |
| 6,424,416 B1 * | 7/2002 | Gross ....................... | G01J 3/46 356/419 |
| 6,553,852 B1 | 4/2003 | Small et al. | |
| 6,753,966 B2 * | 6/2004 | Von Rosenberg .......................... | G01N 21/8507 356/432 |
| 6,961,490 B2 * | 11/2005 | Maisenhoelder .... | G01N 21/552 385/37 |
| 7,276,368 B2 * | 10/2007 | Saaski .................. | G01N 21/553 436/805 |
| 7,496,245 B2 * | 2/2009 | Saaski .................. | G02B 6/4206 250/227.14 |
| 8,269,161 B2 * | 9/2012 | Schaefer ............ | G01N 21/8507 250/258 |
| 8,325,336 B2 | 12/2012 | Preiner et al. | |
| 8,444,937 B2 | 5/2013 | Tuli et al. | |
| 8,445,841 B2 * | 5/2013 | Szobota ............... | G01N 21/552 250/254 |
| 8,675,199 B2 * | 3/2014 | Duer .................... | G02B 6/4226 385/12 |
| 9,423,397 B2 * | 8/2016 | Duer .................... | G01N 21/648 |
| 9,976,192 B2 * | 5/2018 | Duer .................. | G01N 21/6428 |
| 10,337,159 B2 * | 7/2019 | Morgan ............. | G01N 21/8507 |
| 10,337,283 B2 | 7/2019 | Gottumukkala et al. | |
| 10,345,283 B1 * | 7/2019 | Laird .................... | G01N 21/552 |
| 10,458,907 B2 | 10/2019 | Roodenko | |
| 11,156,561 B2 * | 10/2021 | Mannhardt .......... | G01N 21/552 |
| 11,808,913 B2 * | 11/2023 | Mangeat ............. | G01N 21/8507 |
| 2002/0039186 A1 | 4/2002 | Rosenberg | |
| 2010/0148785 A1 | 6/2010 | Schaefer et al. | |
| 2010/0309463 A1 | 12/2010 | Lucke et al. | |
| 2012/0170023 A1 | 7/2012 | Szobota et al. | |
| 2017/0370064 A1 | 12/2017 | Morgan et al. | |
| 2018/0306726 A1 | 10/2018 | Mannhardt et al. | |
| 2019/0285608 A1 | 9/2019 | Laird et al. | |
| 2023/0384476 A1 | 11/2023 | Mangeat et al. | |

FOREIGN PATENT DOCUMENTS

| | | |
|---|---|---|
| DE | 112015002036 T5 | 7/2017 |
| EP | 1484600 A2 | 12/2004 |
| EP | 1264170 B1 | 2/2009 |
| EP | 2429942 | 3/2012 |
| EP | 3395147 A1 | 10/2018 |
| WO | WO 2017187088 A1 | 11/2017 |
| WO | 2017223435 A1 | 12/2017 |
| WO | WO 2018112116 A1 | 6/2018 |
| WO | 2018146352 A1 | 8/2018 |
| WO | WO 2021168574 A1 | 9/2021 |

OTHER PUBLICATIONS

Ackerson, Jason P., C.L.S. Morgan, and Y. Ge, "Penetrometer-mounted VisNIR spectroscopy: Application of EPO-PLS to in situ VisNIR spectra," Geoderma 286 (2017): 131-138 (Year :2017), 8 pages.
Extended European Search Report of EP 19861506.4, dated May 4, 2022, 7 pages filed herewith.
PCT "International Search Report" for PCT/CA2019/051322 of Dec. 12, 2019, 4 pages.
PCT "Written Opinion" for PCT/CA2019/051322 of Dec. 12, 2019, 5 pages.
PCT "International Preliminary Report on Patentability" for PCT/CA2019/051322 of Mar. 23, 2021, 6 pages.
PCT "International Search Report" for PCT/CA2021/050233 dated May 4, 2021, 3 pages.
PCT "Written Opinion" for PCT/CA2021/050233 dated May 4, 2021, 3 pages.
Extended European search report (EESR) for Application No. EP 21760108.7, "Optical Probe and Method for Real-Time and In-Situ Measurements of Soil Properties", dated May 3, 2024, 8 pages.

* cited by examiner

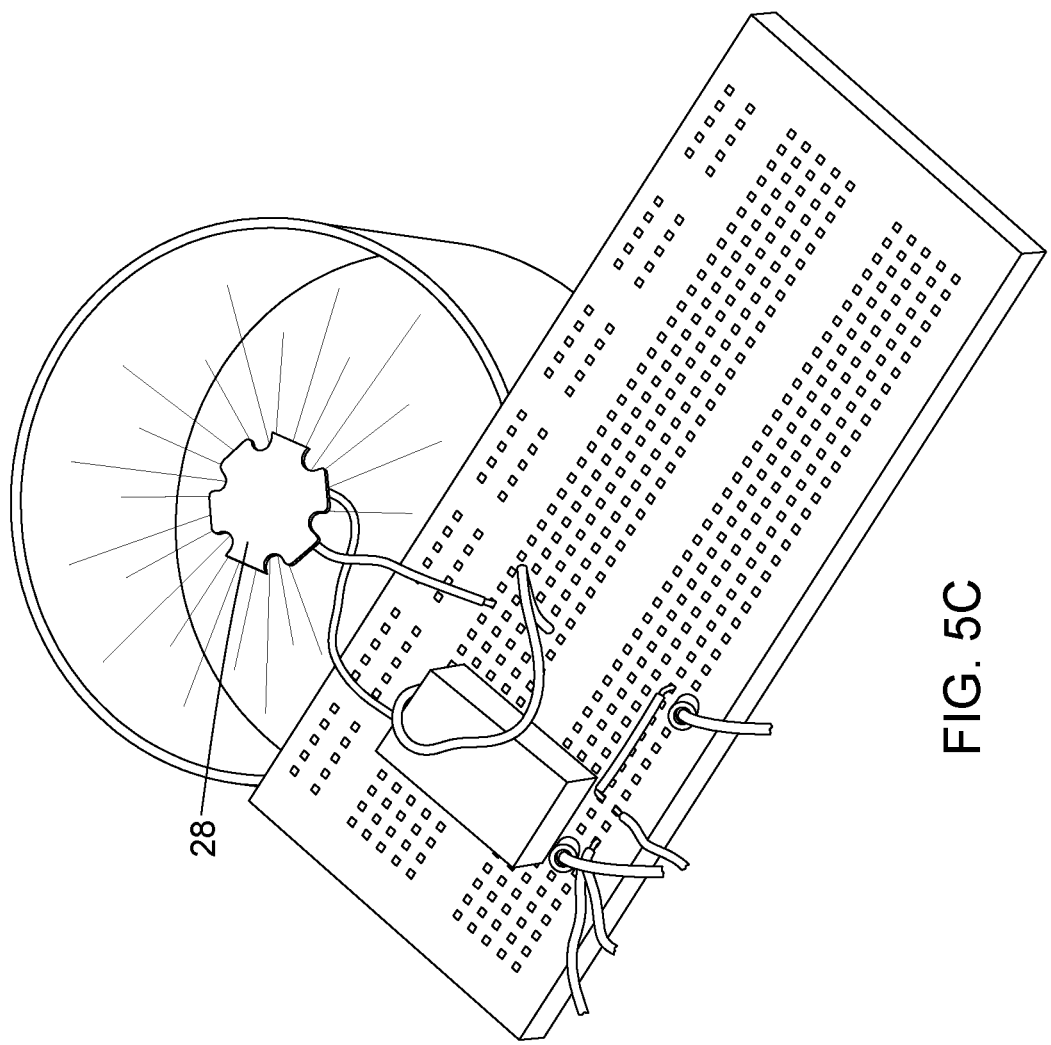
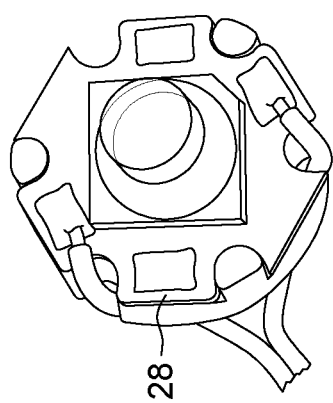
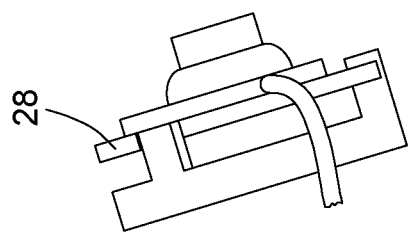
FIG. 5C
FIG. 5A
FIG. 5B

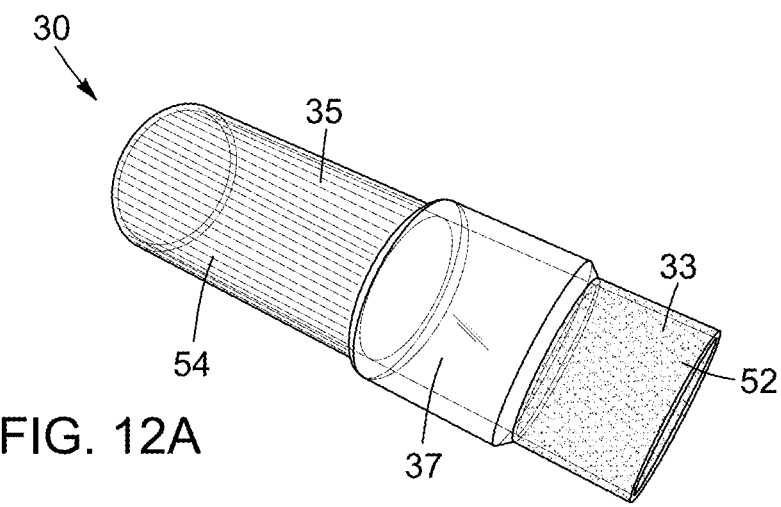
FIG. 12A
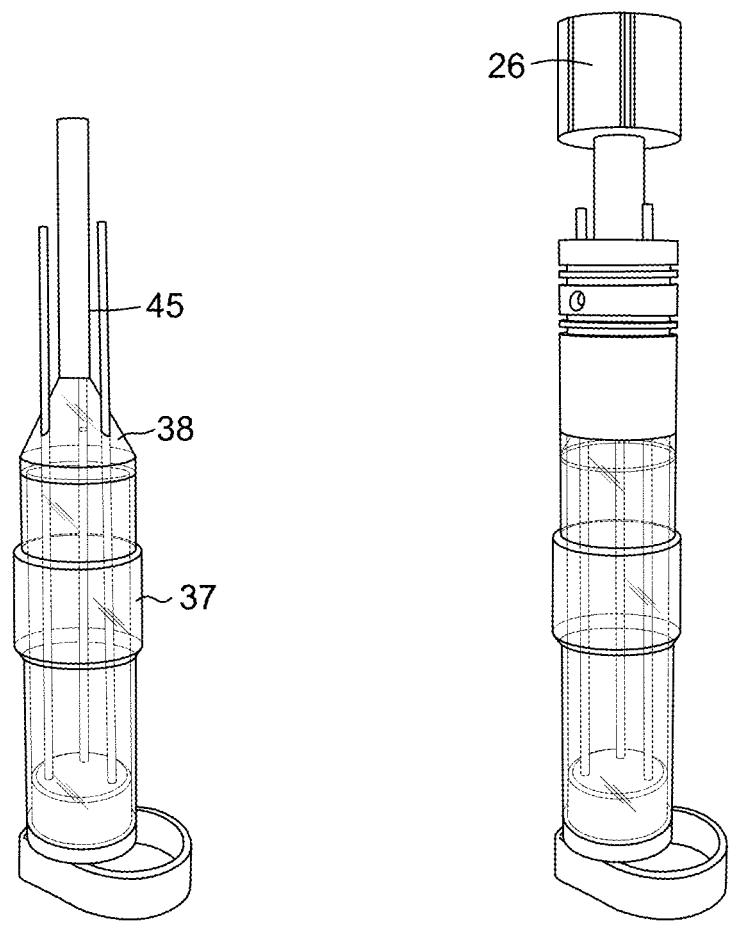
FIG. 12B
FIG. 12C

OPTICAL PROBE COMPRISING A WAVEGUIDE AND METHOD FOR REAL-TIME AND IN-SITU MEASUREMENTS OF SOIL PROPERTIES

CROSS-REFERENCE TO RELATED APPLICATIONS

This application is a National Stage of International Application No. PCT/CA2021/050233, "OPTICAL PROBE AND METHOD FOR REAL-TIME AND IN-SITU MEASUREMENTS OF SOIL PROPERTIES", filed Feb. 25, 2021, which claims the benefit of U.S. Provisional Application No. 62/981,729, filed Feb. 26, 2020, both of which are incorporated herein by reference.

TECHNICAL FIELD

The technical field generally relates to systems and methods for measuring soil properties, and more particularly concerns techniques for diffuse real-time and in-situ measurements of soil properties.

BACKGROUND

Soil tests have been historically performed in a laboratory. Several soil samples are typically collected, which may be achieved by extracting the samples from a field. Once the samples have been extracted, they are sent to the laboratory for subsequent analyses and characterization.

It is known that the characteristics of a soil sample may change or evolve over time. For instance, some characteristics of the extracted samples may be altered during their transport or when they are stored. Thus, the results of the analyses performed on such altered soil samples may not be representative of the actual soil characteristics in situ. The characteristics of the soil also can also vary within the same field. As laboratory characterizations are time consuming and generally expensive, only one laboratory analysis is traditionally performed per field, resulting in a relatively poor characterization of the field.

There is thus a need for a system, device, as well as methods that address or alleviate at least some of the challenges presented above.

SUMMARY

In accordance with one aspect, there is provided an optical probe for analysing a soil located in an underground area, the optical probe including: a light source configured to generate a multiwavelength interrogating beam; a probe head insertable into the underground area to contact the soil, the probe head including a waveguide, the waveguide including: a first end optically shielded from the soil and optically coupled with the light source, the first end being configured to receive the multiwavelength interrogating beam, the multiwavelength interrogating beam being guided in the waveguide; a second end optically shielded from the soil, the second end being opposite the first end; and an interaction zone located between the first end and the second end, the interaction zone being optically coupled with the soil when the probe head is inserted in the underground area and being configured to receive the multiwavelength interrogating beam from the first end, an evanescent portion of the multiwavelength interrogating beam propagating outside from the waveguide and interacting with the soil, thereby leaving an attenuated portion of the multiwavelength interrogating beam in the waveguide, the attenuated portion of the multiwavelength interrogating beam being guided towards the second end; a detector optically coupled with the waveguide near or at the second end, the detector being configured to receive the attenuated portion of the multiwavelength interrogating beam and output a detector signal; and a processor configured to receive the detector signal and determine a spectral content of the evanescent portion of the multiwavelength interrogating beam based on the multiwavelength interrogating beam and the attenuated portion of the multiwavelength interrogating beam, the spectral content being representative of at least one characteristic of the soil.

In some embodiments, the attenuated multiwavelength interrogation beam propagates from the first end towards the second end by total internal reflection.

In some embodiments, the waveguide has a multimode structure configured to guide therein a multimode multiwavelength interrogating beam.

In some embodiments, the multiwavelength interrogating beam has a spectral profile including a waveband extending from about 350 nm to about 900 nm.

In some embodiments, the multiwavelength interrogating beam has a spectral profile including a waveband extending from about 400 nm to about 750 nm.

In some embodiments, the light source includes a stack of light-emitting diodes (LEDs), the stack of LEDs including a first LED having a first spectral profile including a first waveband centered around 550 nm; and a second LED having a second spectral profile including a first waveband centered around 700 nm.

In some embodiments, the waveguide defines a hollow chamber within the probe head.

In some embodiments, the stack of LEDs is substantially aligned with the first end of the waveguide and housed within the hollow chamber.

In some embodiments, the hollow chamber is filled with air.

In some embodiments, the hollow chamber is filled with nitrogen.

In some embodiments, the waveguide includes at least one transparent wall.

In some embodiments, the first end has an outer surface, the outer surface of the first end being coated with a first light-blocking layer.

In some embodiments, the first light-blocking layer is reflective.

In some embodiments, the first light-blocking laser is opaque.

In some embodiments, the second end has an outer surface, the outer surface of the second end being coated with a second light-blocking layer.

In some embodiments, the second light-blocking layer is reflective.

In some embodiments, the second light-blocking layer is opaque.

In some embodiments, the first end includes a first optical structure, the first optical structure being configured to confine and guide the multiwavelength interrogating beam within the first end of the waveguide.

In some embodiments, the first optical structure includes a periodic pattern.

In some embodiments, the periodic pattern includes a plurality of lines.

In some embodiments, the periodic pattern includes an array of points.

In some embodiments, the periodic pattern includes a grating.

In some embodiments, the second end includes a second optical structure, the second optical structure being configured to direct the attenuated portion of the multiwavelength interrogating beam towards the detector.

In some embodiments, the second optical structure includes a periodic pattern.

In some embodiments, the periodic pattern includes a plurality of lines.

In some embodiments, the periodic pattern includes an array of points.

In some embodiments, the periodic pattern includes a grating.

In some embodiments, the waveguide is bubble-shaped in the interaction zone.

In some embodiments, the waveguide is made from a material impermeable to a soil solution present in the soil.

In some embodiments, the waveguide is made from a material selected from the group consisting of clear fused quartz, quartz, sapphire, and acrylic.

In some embodiments, the optical probe further includes an optical element mounted in the probe head and aligned with the second end of the waveguide, the optical element being optically coupled with the second end of the waveguide and being configured to guide the attenuated portion of the multiwavelength interrogating beam from the second end of the waveguide towards the detector.

In some embodiments, the optical element is cone shaped.

In some embodiments, the optical element conforms with an inner surface of the probe head.

In some embodiments, the optical element has a bottom portion, and the second end has a top portion, the bottom portion of the optical element abutting the top portion of the second end.

In some embodiments, the optical element is made from silicone.

In some embodiments, the optical probe further includes an optical fiber positioned between the optical element and the detector, the optical fiber being configured to optically couple the detector with the optical element.

In some embodiments, the optical probe further includes an optical element, wherein the optical element is integrally formed with the second end of the waveguide, the optical element being configured to guide the attenuated portion of the multiwavelength interrogating beam from the second end of the waveguide towards the detector.

In some embodiments, the optical element is cone shaped.

In some embodiments, the optical element has a bottom portion, and the second end has a top portion, the bottom portion of the optical element being aligned with the top portion of the second end.

In some embodiments, the optical probe further includes an optical fiber positioned between the optical element and the detector, the optical fiber being configured to optically couple the detector with the optical element.

In some embodiments, the optical probe further includes a sensing tip mounted near or at an extremity of the probe head, the sensing tip being configured to measure one of an electroconductivity and a pH of the soil.

In some embodiments, wherein said at least one characteristic of the soil are selected from the group consisting of: level of nutrients, level of available nutrients, ionic concentration of the soil solution, temperature, moisture, pH, level of organic matter and soil texture.

In accordance with another aspect, there is provided an optical probe for analysing a soil located in an underground area, the optical probe including: a probe head insertable into the underground area to contact the soil, the probe head including a waveguide having opposite first and second ends both optically shielded from the soil; a light source configured to generate a multiwavelength interrogating beam and optically coupled to the first end of the waveguide so that the multiwavelength interrogation beam is inputted in the waveguide to propagate towards the second end; and a detector optically coupled to the second end of the waveguide to detect said multiwavelength interrogation beam; wherein the waveguide includes an unshielded interaction zone extending between the first and second ends providing a wavelength-dependent attenuation of the multiwavelength interrogation beam through interaction with the soil.

In some embodiments, the optical probe further includes a processor receiving a detector signal from the detector and configured to evaluate therefrom the wavelength-dependent attenuation of the multiwavelength interrogation beam, said wavelength-dependent attenuation of the multiwavelength interrogation beam being representative of at least one characteristic of the soil.

In some embodiments, the attenuated multiwavelength interrogation beam propagates from the first end towards the second end by total internal reflection.

In some embodiments, the waveguide has a multimode structure configured to guide therein a multimode multiwavelength interrogating beam.

In some embodiments, the multiwavelength interrogating beam has a spectral profile including a waveband extending from about 350 nm to about 900 nm.

In some embodiments, the multiwavelength interrogating beam has a spectral profile including a waveband extending from about 400 nm to about 750 nm.

In some embodiments, the light source includes a stack of light-emitting diodes (LEDs), the stack of LEDs including: a first LED having a first spectral profile including a first waveband centered around 550 nm; and a second LED having a second spectral profile including a first waveband centered around 700 nm.

In some embodiments, the waveguide defines a hollow chamber within the probe head.

In some embodiments, the stack of LEDs is substantially aligned with the first end of the waveguide and housed within the hollow chamber.

In some embodiments, the hollow chamber is filled with air.

In some embodiments, the hollow chamber is filled with nitrogen.

In some embodiments, the waveguide includes at least one transparent wall.

In some embodiments, the first end has an outer surface, the outer surface of the first end being coated with a first light-blocking layer.

In some embodiments, the first light-blocking layer is reflective.

In some embodiments, the first light-blocking layer is opaque.

In some embodiments, the second end has an outer surface, the outer surface of the second end being coated with a second light-blocking layer.

In some embodiments, the second light-blocking layer is reflective.

In some embodiments, the second light-blocking layer is opaque.

In some embodiments, the first end includes a first optical structure, the first optical structure being configured to confine and guide the multiwavelength interrogating beam within the first end of the waveguide.

In some embodiments, the first optical structure includes a periodic pattern.

In some embodiments, the periodic pattern includes a plurality of lines.

In some embodiments, the periodic pattern includes an army of points.

In some embodiments, the periodic pattern includes a grating.

In some embodiments, the second end includes a second optical structure, the second optical structure being configured to direct the attenuated portion of the multiwavelength interrogating beam towards the detector.

In some embodiments, the second optical structure includes a periodic pattern.

In some embodiments, the periodic pattern includes a plurality of lines.

In some embodiments, the periodic pattern includes an array of points.

In some embodiments, the periodic pattern includes a grating.

In some embodiments, the waveguide is bubble-shaped in the interaction zone.

In some embodiments, the waveguide is made from a material impermeable to a soil solution present in the soil.

In some embodiments, the waveguide is made from a material selected from the group consisting of: clear fined quartz, quartz, sapphire, and acrylic.

In some embodiments, the optical probe further includes an optical element mounted in the probe head and aligned with the second end of the waveguide, the optical element being optically coupled with the second end of the waveguide and being configured to guide the attenuated portion of the multiwavelength interrogating beam from the second end of the waveguide towards the detector.

In some embodiments, the optical element is cone shaped.

In some embodiments, the optical element conforms with an inner surface of the probe head.

In some embodiments, the optical element has a bottom portion, and the second end has a top portion, the bottom portion of the optical element abutting the top portion of the second end.

In some embodiments, the optical element is made from silicone.

In some embodiments, the optical probe further includes an optical fiber positioned between the optical element and the detector, the optical fiber being configured to optically couple the detector with the optical element.

In some embodiments, the optical probe further includes an optical element, wherein the optical element is integrally formed with the second end of the waveguide, the optical element being configured to guide the attenuated portion of the multiwavelength interrogating beam from the second end of the waveguide towards the detector.

In some embodiments, the optical element is cone shaped.

In some embodiments, the optical element has a bottom portion, and the second end has a top portion, the bottom portion of the optical element being aligned with the top portion of the second end.

In some embodiments, the optical probe further includes an optical fiber positioned between the optical element and the detector, the optical fiber being configured to optically couple the detector with the optical element.

In some embodiments, the optical probe further includes a sensing tip mounted near or at an extremity of the probe head, the sensing tip being configured to measure one of an electroconductivity and a pH of the soil.

In some embodiments, said at least one characteristic of the soil are selected from the group consisting of level of nutrients, level of available nutrients, ionic concentration of the soil solution, temperature, moisture, pH, level of organic matter and soil texture.

In accordance with another aspect, there is provided a method for analysing a soil located in an underground area, the method including steps of: inserting a probe head in the underground area to contact the soil, the probe head including a waveguide, the waveguide including a first end, a second end opposite the first end and an interaction zone located between the first end and the second end; projecting a multiwavelength interrogating beam towards the first end; guiding, in the waveguide, the multiwavelength interrogating beam, an evanescent portion of the multiwavelength interrogating beam propagating outside from the waveguide and interacting with the soil in the interaction zone, thereby producing an attenuated portion of the multiwavelength interrogating beam in the waveguide, the attenuated portion of the multiwavelength interrogating beam being guided towards the second end; detecting the attenuated portion of the multiwavelength interrogating beam; and determining a spectral content of the evanescent portion of the multiwavelength interrogating beam based on the multiwavelength interrogating beam and the attenuated portion of the multiwavelength interrogating beam, the spectral content being representative of at least one characteristic of the soil.

In some embodiments, the attenuated multiwavelength interrogation beam propagates from the first end towards the second end by total internal reflection by total internal reflection.

In some embodiments, said at least one characteristic of the soil are selected from the group consisting of level of nutrients, level of available nutrients, ionic concentration of the soil solution, temperature, moisture, pH, level of organic matter and soil texture.

In some embodiments, the method further includes measuring at least one of an electroconductivity and a pH of the soil with a sensing tip mounted near or at an extremity of the probe head.

In some embodiments, said determining the spectral content of the evanescent portion of the multiwavelength interrogating beam includes producing an output signal representative of the at least one characteristic of the soil and processing the output signal.

In some embodiments, said inserting the probe head in the underground area to contact the soil includes insetting the probe head at a depth ranging from about 0 cm to about 80 cm under the soil surface.

Other features and advantages of the present description will become more apparent upon reading of the following non-restrictive description of specific embodiments thereof, given by way of example only with reference to the accompanying drawings.

BRIEF DESCRIPTION OF THE DRAWINGS

FIGS. 5A-C illustrate one of the light-emitting diodes of FIG. 4.

FIGS. 12A-C illustrate a waveguide having a bubble-shaped interaction zone, in accordance with one embodiment.

DETAILED DESCRIPTION

Figure 1:
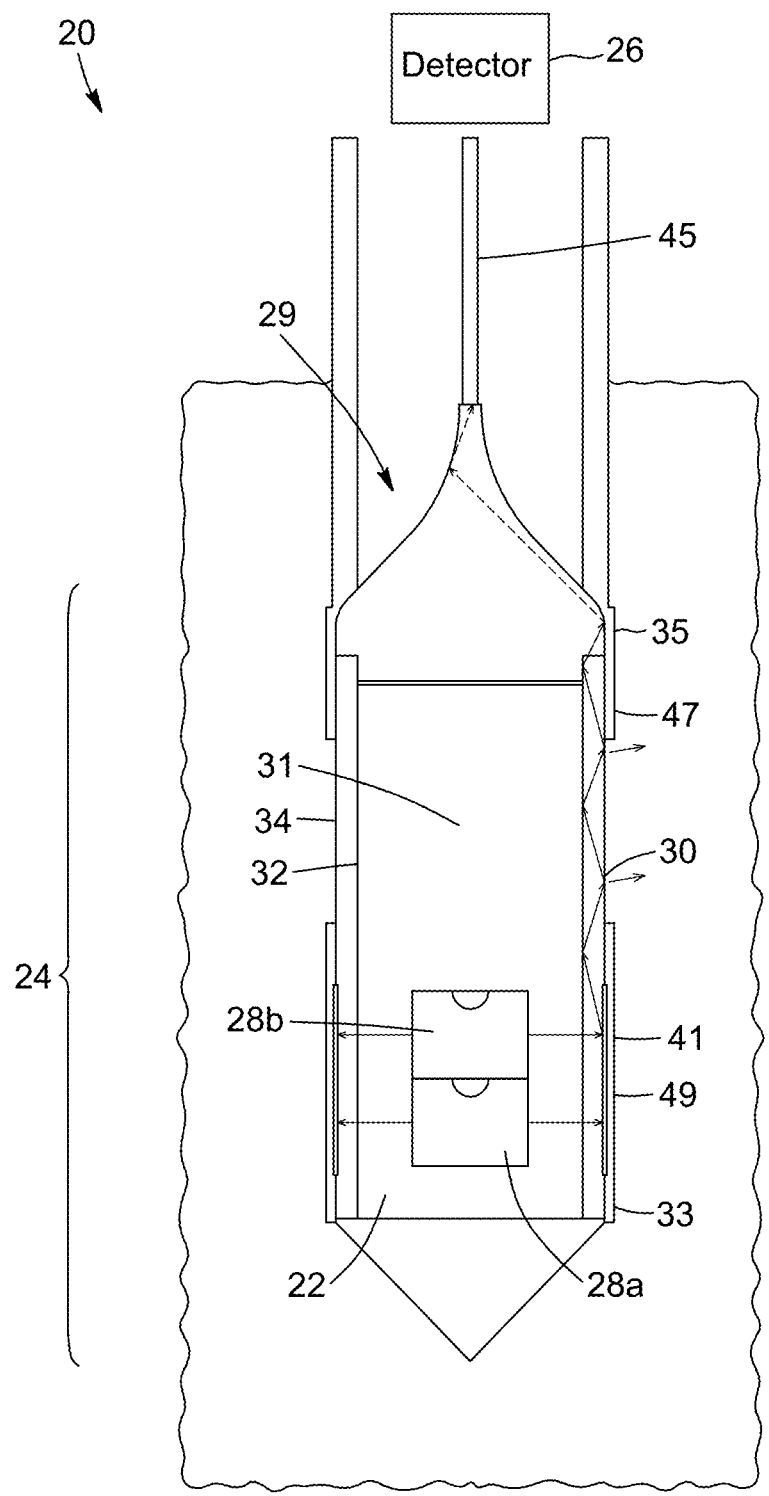
FIG. 1 is a side view of a probe head, in accordance with one embodiment.

In the following description, similar features in the drawings have been given similar reference numerals, and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments.

The terms "a", "an" and "one" are defined herein to mean "at least one", that is, these terms do not exclude a plural number of elements, unless stated otherwise. It should also be noted that terms such as "substantially", "generally" and "about", that modify a value, condition, or characteristic of a feature of an exemplary embodiment, should be understood to mean that the value, condition or characteristic is defined within tolerances that are acceptable for the proper operation of this exemplary embodiment for its intended application.

In the present description, the terms "connected". "coupled", and variants and derivatives thereof, refer to any connection or coupling, either direct or indirect, between two or more elements. The connection or coupling between the elements may be acoustical, mechanical, physical, optical, operational, electrical, wireless, or a combination thereof.

In the present description, the expression "based on" is intended to mean "based at least partly on", that is, this expression can mean "based solely on" or "based partially on", and so should not be interpreted in a limited manner. More particularly, the expression "based on" could also be understood as meaning "depending on", "representative of", "indicative of", "associated with" or similar expressions.

In the present description, the terms "light" and "optical", and variants and derivatives thereof, are used to refer to radiation in any appropriate region of the electromagnetic spectrum. The terms "light" and "optical" are therefore not limited to visible light, but can also include, without being limited to, the infrared and ultraviolet regions. For example, in some implementations, the present techniques can be used with electromagnetic signals having wavelengths ranging from about 300 nm to 900 nm, and, for example, between 340 nm et 880 nm. However, this range is provided for illustrative purposes only and some implementations of the present techniques may operate outside this range. Also, the skilled person will appreciate that the definition of the ultraviolet, visible and infrared ranges in terms of spectral ranges, as well as the dividing lines between them, can vary depending on the technical field or the definitions under consideration, and are not meant to limit the scope of applications of the present techniques.

It will be appreciated that positional descriptors indicating the position or orientation of one element with respect to another element are used herein for ease and clarity of description and should, unless otherwise indicated, be taken in the context of the figures, and should not be considered limiting. It will be understood that spatially relative terms (e.g., "outer" and "inner", "outside" and "inside" and "top" and "bottom") are intended to encompass different positions and orientations in use or operation of the present embodiments, in addition to the positions and orientations exemplified in the figures.

The term "field" is herein used to refer to a region of land where trees, plants, crops and the like usually grow. The term "soil" is herein used for qualifying the underground area beneath the surface of the field, which may include the surface or a portion thereof. It should be noted that the expressions "trees", "plants", "crops", synonyms and derivatives thereof may encompass a broad variety of organisms and should not be considered limitative. Nonlimitative examples of trees, plants or crops may include seedlings, ornamental crops, ornamental plants, plugs, liners, fruits, small fruits, vegetables, leafy greens, herbs, young plants, high-value crops, perennial plants, annual plants, biennial plants, grain, grass, cereal, and many others. The trees, plants or crops may be produced for human food, non-human food, or non-food applications. Of note, the present techniques may be used to characterize different substrates such as, for example and without being limitative: compost, manure, food, and/or plants. Of course, these examples are nonlimitative and serve an illustrative purpose only.

Optical Probe

Broadly described, there is provided an optical probe for analysing a soil located in an underground area of a field using spectroscopy. The optical probe allows assessing in real time, or near real time, different characteristics of the soil, which are globally referred to as "the soil condition" in the present description. These characteristics include but are not limited to level of nutrients present in the soil, temperature, moisture, pH, level of organic matter and ionic concentration of the soil solution. The optical probe broadly relies on spectroscopy, i.e., the production and investigation of spectra for determining the soil condition. The spectra are collected, obtained, determined, produced, or calculated after the interaction of a multiwavelength interrogating beam (or a portion thereof) with the soil (or a portion thereof). More specifically, a multiwavelength interrogating beam is generated and guided in a waveguide. The waveguide may be made from a substantially clear material having a relatively high refractive index. The waveguide is inserted in the soil and the clear material is put in contact with the soil. A portion of the interrogating beam will be absorbed by the soil contacting the waveguide. In the current disclosure, the absorbed portion of the generated light may be referred to as an evanescent wave, which is representative of at least one characteristics of the soil. The attenuated portion of the interrogating beam is then detected using a spectral or a non-spectral detector. The present techniques allow determining a spectral content or any other relevant properties of the evanescent wave, based on the interrogating beam and the attenuated portion of the interrogating beam.

The optical probe can be inserted in the underground area of a field to measure and monitor the soil condition in situ, i.e., without the need to extract a soil sample from the field prior to its characterization, thereby providing a dynamic characterization of the soil, instead of a single static measurement of the soil condition, which is typically obtained in a laboratory. In some embodiments, the optical probe can be sequentially moved from one location to another to take measurements at different locations of the field being characterized, thereby allowing to obtain a global representation (i.e., a "cartography") of the field. In some embodiments, a plurality of optical probes may be installed in the field, and the cartography of the field is obtained by combining the measurements and results collected with each optical probe. The measurements obtained with the present optical probe have a relatively high spatial precision, in comparison with existing solutions.

In some embodiments, the dynamic characterization of the soil may be used to plan the maintenance of the field, plan the fertilization of the field, evaluate, and potentially prevent the risk of diseases for the tree(s), plant(s) and/or crop(s) growing in the field, and the like.

Figure 2:
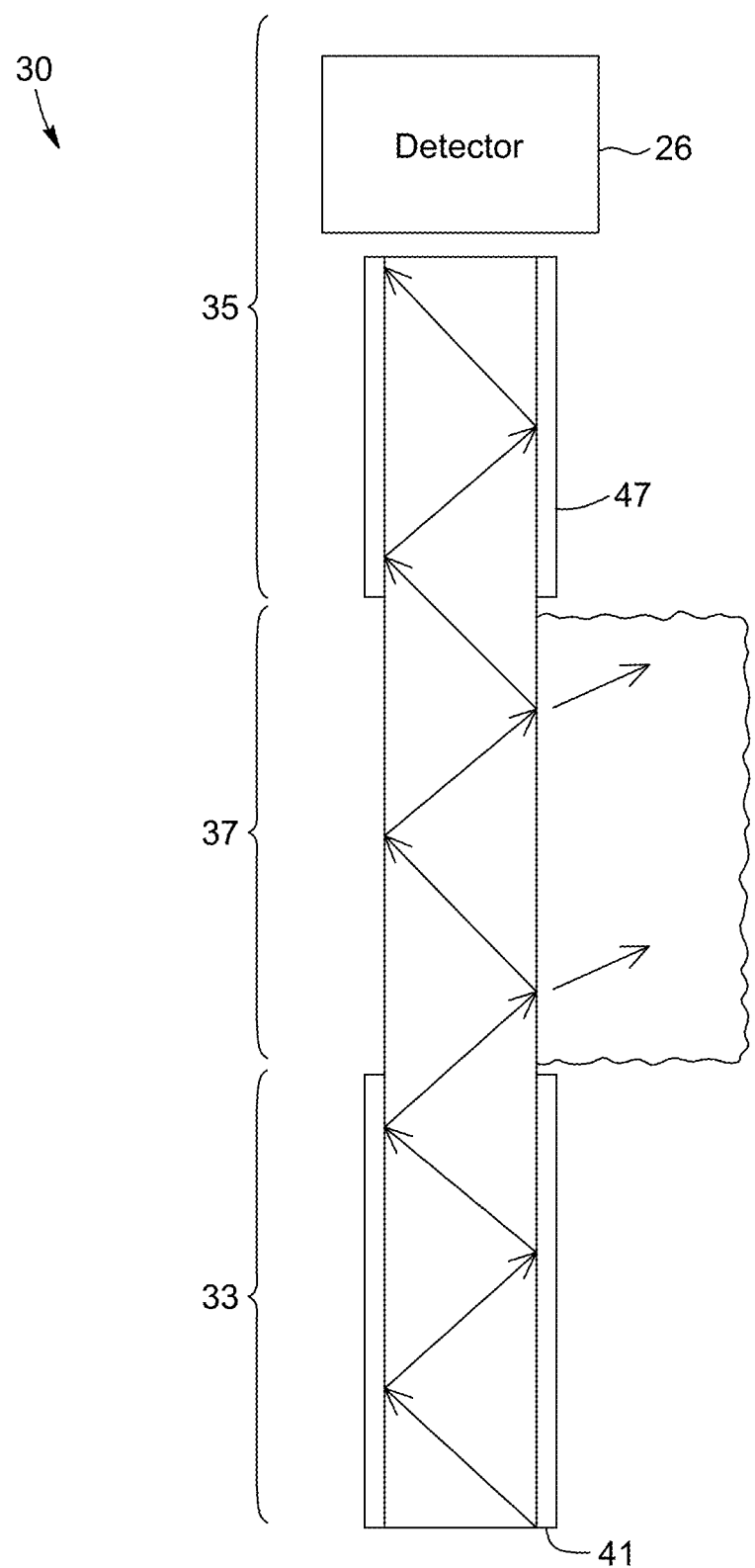
FIG. 2 shows the propagation of a multiwavelength interrogating beam in a waveguide and the interaction of the multiwavelength interrogating beam with the soil
Figure 3:
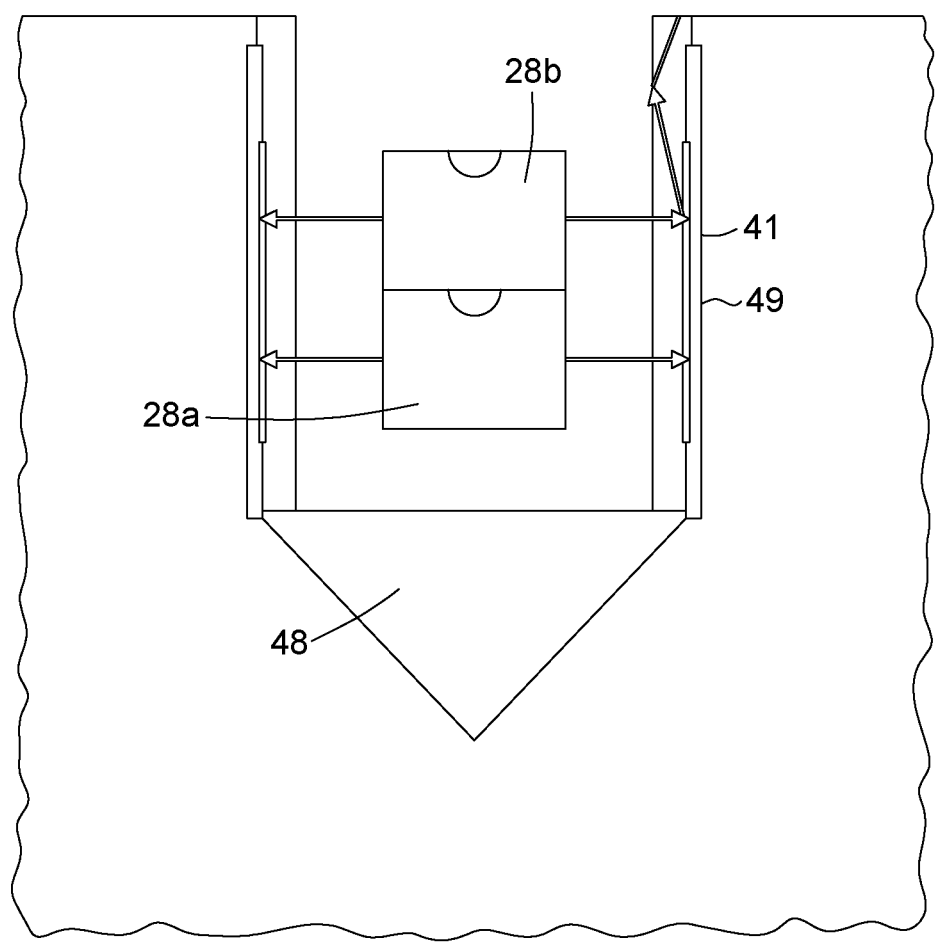
FIG. 3 shows a bottom portion of an optical probe, in accordance with one embodiment.

Now turning to FIGS. 1 to 3, there is illustrated an optical probe 20 for analysing a soil located in an underground area. The optical probe 20 includes a probe head 24 insertable into the underground area to contact the soil. The probe head 24 includes a waveguide 30 having opposite first and second ends 33, 35, both being optically shielded from the soil. The waveguide 30 includes an unshielded interaction zone 37 extending between the first and second ends 33,35, providing a wavelength-dependent attenuation of the multiwavelength interrogation beam through interaction with the soil. The optical probe 20 includes a light source 22 configured to generate a multiwavelength interrogating beam. The light source 22 is optically coupled to the first end 33 of the waveguide 30 so that the multiwavelength interrogation beam is inputted in the waveguide 30 to propagate towards the second end 35. In some embodiments, the multiwavelength interrogation beam propagates from the first end 33 towards the second end 35 by total internal reflection. The optical probe 20 includes a detector 26 optically coupled to the second end 35 of the waveguide 30. The detector 26 is configured to receive an attenuated portion of the multiwavelength interrogation beam.

Figure 15A:
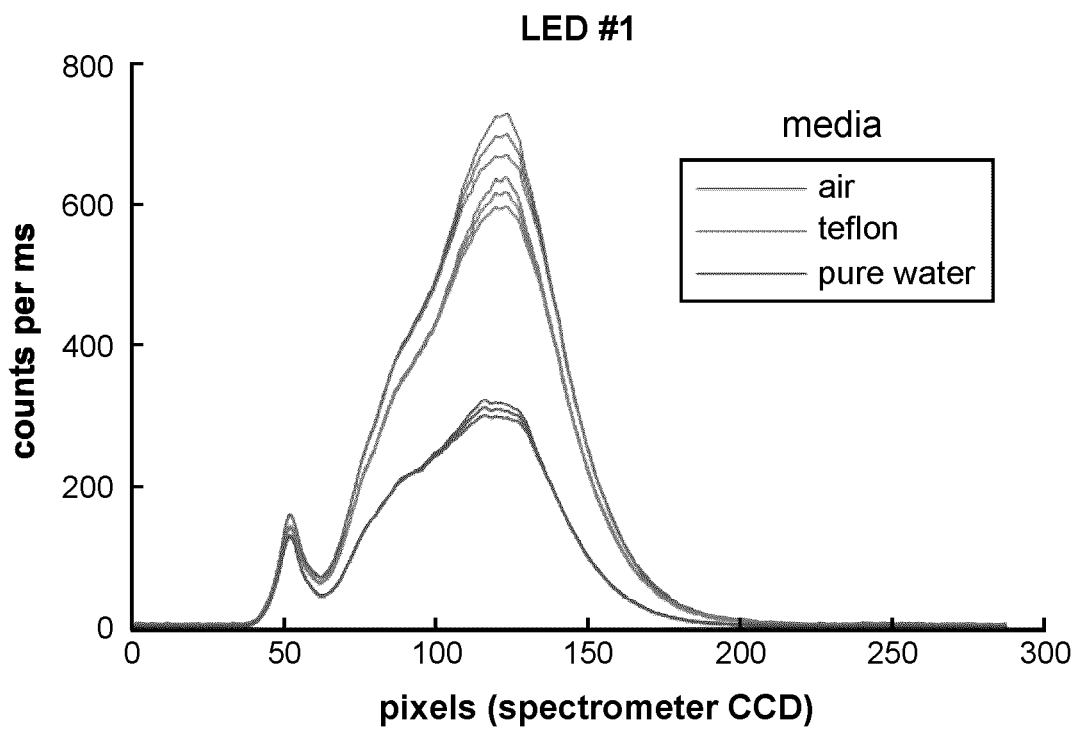
FIGS. 15A-B show the spectral profile LEDs used as a light source, in accordance with one embodiment.
Figure 15B:
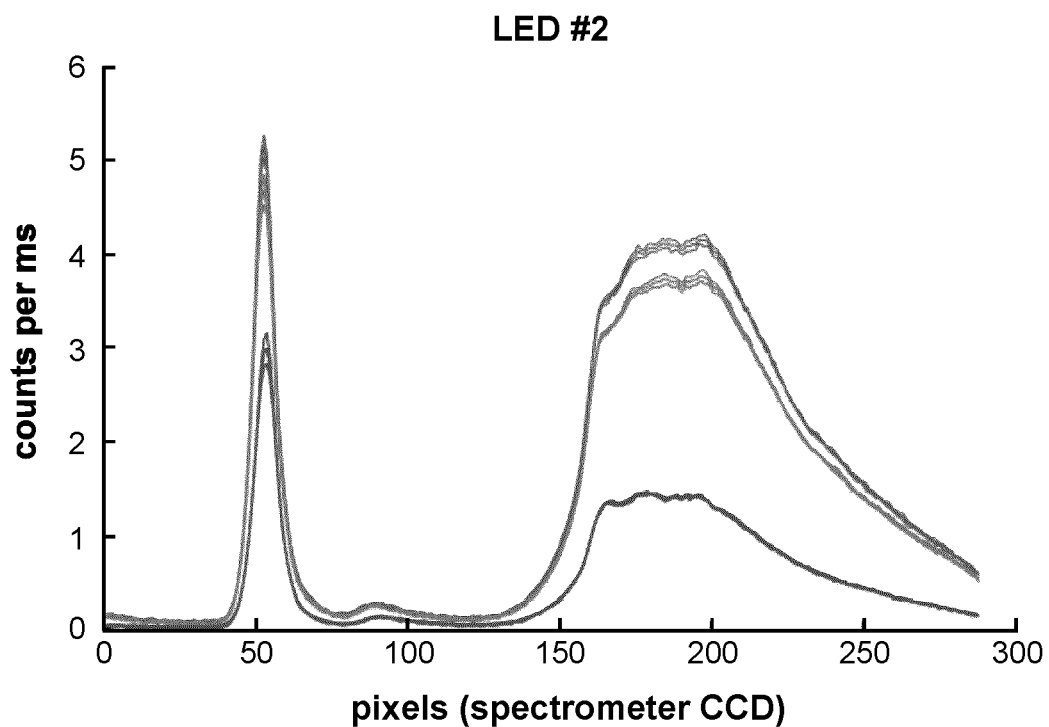
Figure 15C:
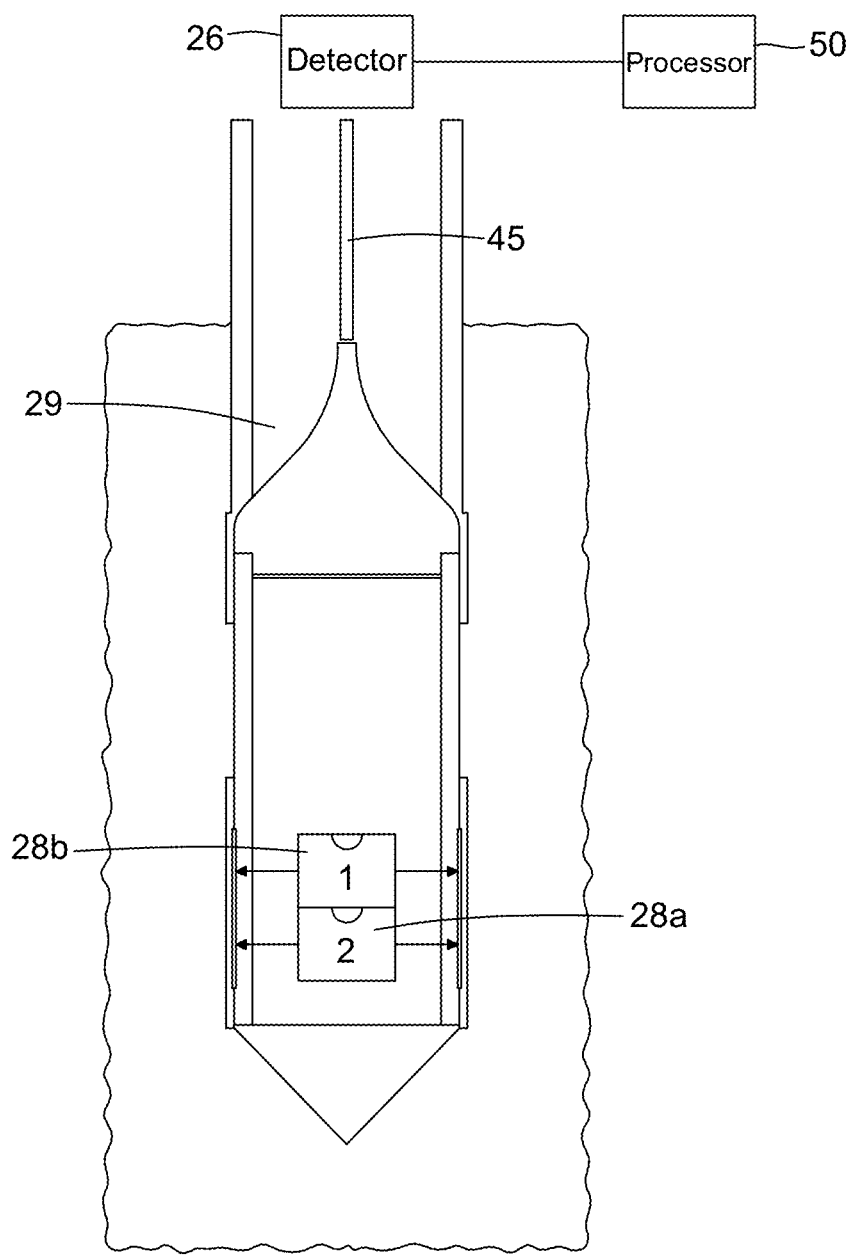
FIG. 15C is a side view of an optical probe including a processor, in according with one embodiment.
Figure 16B:
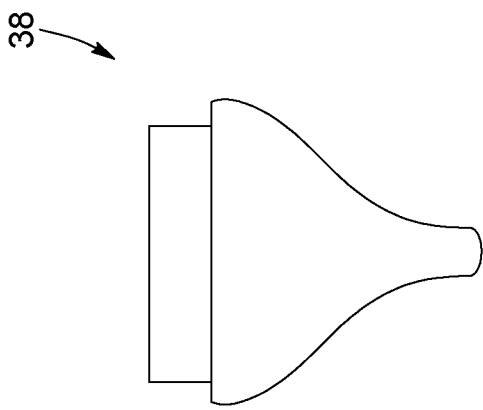
FIGS. 16A-C show different views of a cone-shaped silicone optical element.
Figure 16C:
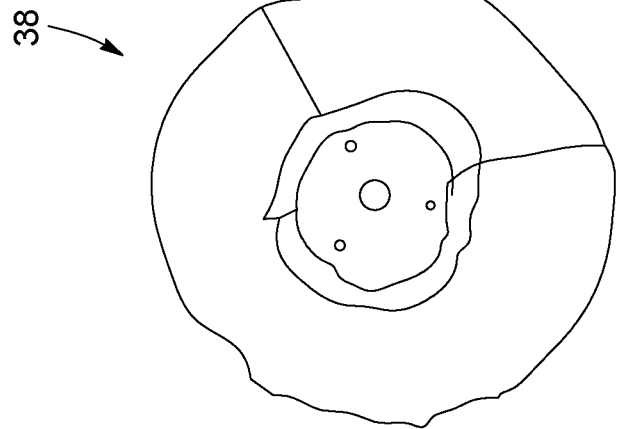
Figure 16A:
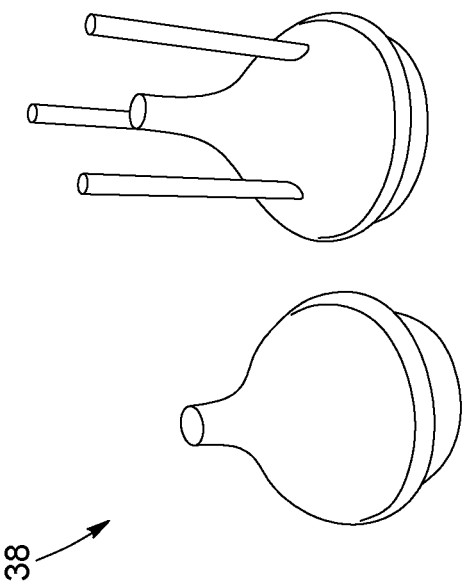

In some embodiments, such as the one illustrated in FIG. 15C, the optical probe 20 may include a processor 50 receiving a detector signal from the detector 26. In these embodiments, the processor 50 is configured to evaluate therefrom the wavelength-dependent attenuation of the multiwavelength interrogation beam. The wavelength-dependent attenuation of the multiwavelength interrogation beam is representative of at least one characteristic of the soil.

Now that the general structure of the optical probe 20 has been succinctly described, different embodiments of the light source 22, the probe head 24, the detector 26, the waveguide 30 and the processor 50 will now be presented.

The light source 22 is configured to generate a multi wavelength interrogating beam. The expression "interrogating beam" is used throughout the description and refers to the beam produced by the tight source 22 that will eventually interact with the soil or a portion thereof. As it will be explained in greater detail below, the interaction between the interrogating beam or a portion thereof provides information about the soil condition. The expression "multiwavelength" refers to the spectral content of the interrogating beam and is more particularly used to refer to the fact that the interrogating beam includes uses, involves or is composed of multiple wavelengths.

The multiwavelength interrogating beam has a spectral profile which can be obtained with one or more light emitters. In some embodiments, the spectral profile of the multiwavelength interrogating beam may be relatively broad, i.e., the spectral profile covers a relatively large portion of the electromagnetic spectrum. In some embodiments, the spectral profile of the multiwavelength interrogating beam may be relatively narrow, i.e., covers only one or more portions (or "waveband(s)") of the electromagnetic spectrum. The combination of different light sources or emitters may be useful to extend the overall bandwidth of the emission spectrum and/or to maximize the relative power of some portions of the emission spectrum. In the context of soil analysis applications, different wavelengths or different wavebands can serve different purposes. For example, and without being limitative, visible, infrared, and blue light can be useful for detecting level of nutrients, level of available nutrients, ionic concentration of the soil solution, temperature, moisture, pH, level of organic matter and soil texture. Ultra-violet (UV) light can be useful for fluorescent matter, mineral and/or organic. In some embodiments, the spectral profile comprises a waveband ranging from about 350 nm to about 900 nm. In other embodiments, the spectral profile of the illuminating could comprise a visible waveband ranging from about 400 nm to about 750 nm.

In some embodiments, such as the ones illustrated in FIGS. 3 to 6 and 15C, the light source 22 may include a plurality of sub-sources, each generating a corresponding sub-beam. The sub-beams can be combined to obtain the multiwavelength interrogating beam. In some embodiments, each sub-source may include one or more light-emitting diodes (LEDs) 28. In the embodiment depicted in FIG. 3, the light source 22 includes two LEDs 28a,b. Of note, the light source 22 may alternatively or additionally include, for example and without being limitative, a solid-state lighting source, including lasers, organic LEDs (OLEDs), incandescent lighting, halogen lighting, fluorescent light, infrared heat emitters, discharge lighting, combinations thereof or the like. In some embodiments the light source 22 may include any light-emitting device that converts electrical energy into electromagnetic radiation through the recombination of electronic carriers (i.e., electrons and holes) in a light emitting layer or region. The emitting layer or region may include, but is not limited to, silicon, silicon carbide, gallium nitride and/or other semiconductor materials, and may or may not include a substrate such as sapphire, silicon, silicon carbide and/or other microelectronic substrates. The light source 22 may include both inorganic and organic light emitters, many of which are known to the skilled person and need not be described in detail herein. Non-limiting examples of light source 22 includes semiconductor light-emitting diodes (LEDs), semiconductor laser diodes, vertical cavity surface emitting lasers (VCSELs), other semiconductor light emitting devices or lamps, organic light-emitting diodes (OLEDs), and polymer light-emitting diode (PLEDs).

Figure 4:
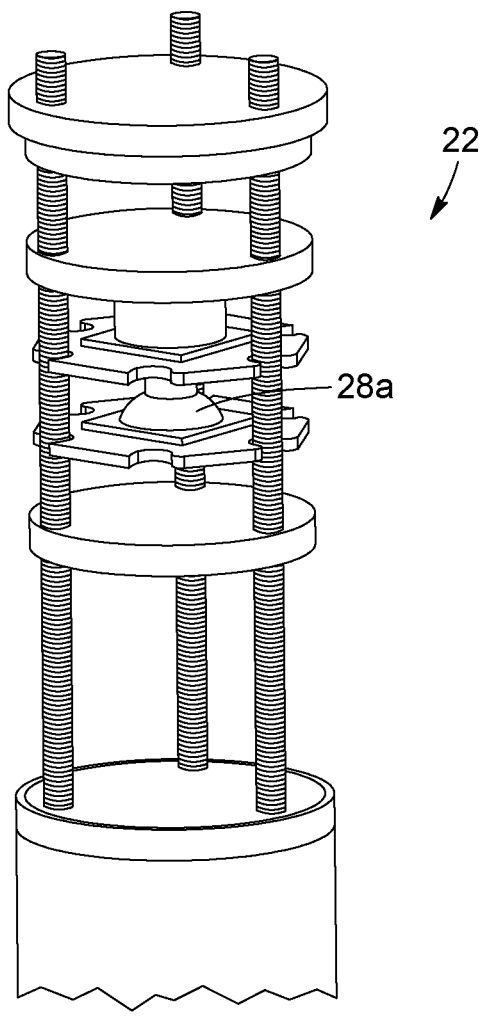
FIG. 4 shows a light source that can be used in an optical probe, in accordance with one embodiment.
Figure 6:
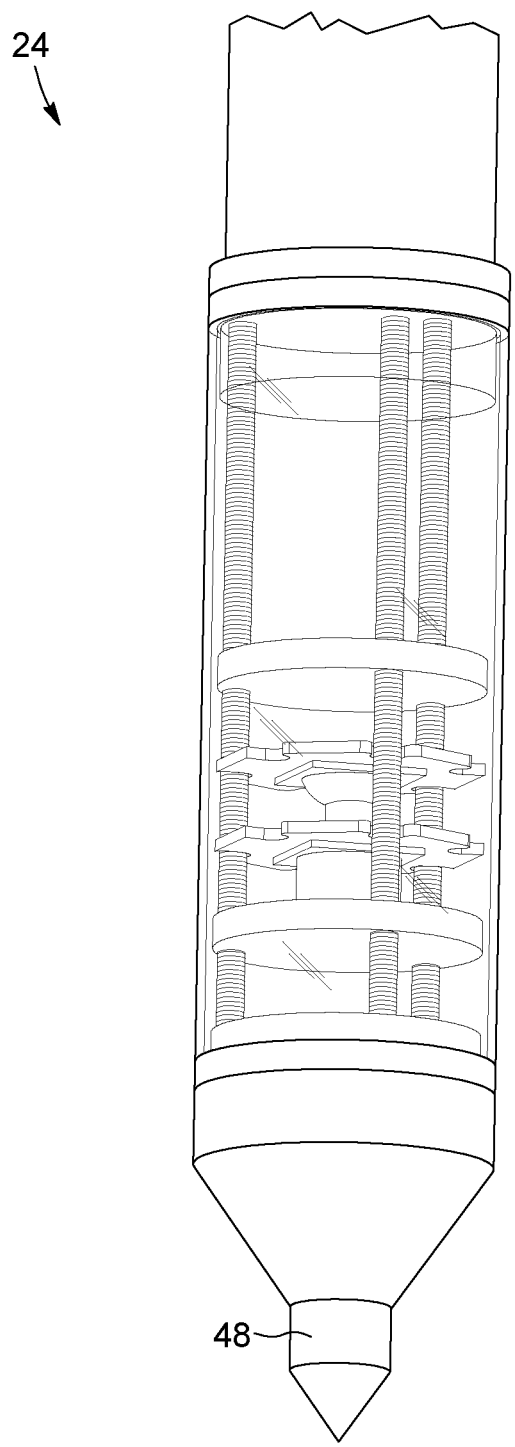
FIG. 6 shows a bottom portion of an optical probe having a sensing tip, in accordance with one embodiment.

In some embodiments, the sub-sources forming the light source 22 may be a stack of LEDs 28a, b, n, wherein n is an integer representative of the number of LEDs in the stack. In some embodiments, the stack of LEDs 28 may include at least one of: a white broad band LED, an infrared broad band LED and/or an ultra-violet LED. In some embodiments, the stack of LEDs 28 may include a first light-emitting diode 28a having a spectral profile comprising a waveband centered around 550 nm and a second light-emitting diode 28b having a spectral profile comprising a waveband centered around 700 nm. Different characteristics of the LEDs 28a,b are illustrated in FIGS. 4 to 6. A nonlimitative example of the positioning of the LEDs 28a,b is illustrated in FIG. 15C. The spectral profile of each of the LEDs 28a,b of FIG. 15C is illustrated in FIGS. 15A-B.

In some embodiments, the waveguide 30 has a multimode structure, i.e., the waveguide 30 is configured such that the multiwavelength interrogating beam being guided therein is a multimode beam. It should be noted that the multimode beam may sometimes be referred to as a "diffuse beam". Of note, the waveguide 30 may have the appropriate dimensions, symmetry, numerical aperture and an other relevant properties for obtaining and guiding the multimode beam.

In some embodiments, the light source 22 is configured for emitting light in a continuous regime. It will however be readily understood that in other embodiments, the light source 22 could be operated either in a continuous regime or an intermittent regime, according to one's needs and/or the targeted application(s). One skilled in the art w ill readily understand that the choice and the configuration of the light source 22 may be limited and/or influenced by the predetermined parameters dictated by a given application. The predetermined parameters include but are not limited to wavelength, power, spatial profile and spectral profile.

Referring back to FIG. 1, the probe head 24 includes a waveguide 30. The probe head 24 is insertable into the underground area to contact the soil. After the insertion of the optical probe 20 in the underground area, the soil surrounds at least a portion of the probe head 24 and the waveguide 30. As illustrated, the soil mechanically contacts the probe head 24 and/or the waveguide 30. It will be noted that there may be a relatively small gap between the soil and the probe head 24.

With reference to FIGS. 1 and 2, the waveguide 30 has a first end 33 and a second end 35. The first end 33 is optically shielded from the soil and optically coupled with the light source 22. The light generated by the light source 22 is inputted in the waveguide 30 through the first end. The first end may therefore be considered an "injection zone" for the multiwavelength interrogating beam. The second end 35 is opposite the first end 33 and is optically shielded from the soil. The expression "optically shielded" herein refers to the absence of or minimal optical interaction(s) between the elements being optically shielded one from another. For example, and without being limitative, in the context of the current description, and as will be explained in greater detail below, the light guided in the first end 33 and/or the second end 35 does not interact with the soil, meaning that the light being guided remains guided and confined in the first end 33 and/or second end 35 of the waveguide 30 and does not propagate outside from the first end 33 and/or second end 35. In some embodiments, the first end 33 and second end 35 are optically insulated or independent from the soil, meaning that the soil does not have an impact on the spectral characteristics of the light being guided in the first end 33 and the second end 35. By contrast, the expression "optically coupled" herein refers to the interaction between the elements being optically coupled one with another.

As illustrated in FIGS. 1 to 3, the waveguide 30 can form a portion or a totality of the probe head 24. In the embodiments illustrated in these Figures, the waveguide 30 includes a tubular transparent wall and defines a hollow chamber 31 within the probe head 24. The hollow chamber 31 is generally confined by an inner surface 32 of the probe head 24. The light source 22 can be mounted in the hollow chamber 31, i.e., in some embodiments, the waveguide 30 encloses the light source 22.

In some embodiments, the hollow chamber 31 may be filled with air or with pure nitrogen. The pure nitrogen can be useful to reduce, minimize or eliminate condensation in the hollow chamber 31. The inner surface 32 and the outer surface 34 of the probe head 24 are relatively topologically smooth, or at least smooth enough to not affect or alter the spectral characteristics of the multiwavelength interrogating beam and/or the attenuated portion of the multiwavelength interrogating beam. In some embodiments, the inner surface 32 and/or the outer surface 34 may be coated with an additional layer or treated with an appropriate physical or chemical process, for example and without being limitative, for enhancing predetermined optical properties, such as the reflexivity or the transmissivity of light.

In some embodiments, the first end 33 comprises a first optical structure 52. The first optical structure 52 is configured to confine and guide the multiwavelength interrogating beam within the first end 33 of the waveguide 30. In some embodiments, the first optical structure 52 comprises a periodic pattern. In some embodiments, the periodic pattern comprises a plurality of lines. In some embodiments, the periodic pattern comprises an array of points. In some embodiments, the periodic pattern comprises a grating.

In some embodiments, the second end 3S comprises a second optical structure 54. The second optical structure 54 is configured to direct the attenuated portion of the multiwavelength interrogating beam towards the detector 26. In some embodiments, the second optical structure 54 comprises a periodic pattern. In some embodiments, the periodic pattern comprises a plurality of lines. In some embodiments, the periodic pattern comprises an array of points. In some embodiments, the periodic pattern comprises a grating.

In some embodiments, such as the one illustrated in FIG. 12A, the first end 33 may include an array of circular voids (herein referred as "points"). Each point has an outer surface and an associated normal vector. In some embodiments, the normal vector forms an angle of approximately 45° with a longitudinal axis of the waveguide 30. It should be noted that the array of points may act as a prism, and so may direct or assist in injecting the multiwavelength interrogating beam in the waveguide 30. The dimensions of the points may be in the micrometric range. For example, the depth of each circular void may be in a range extending between 300 μm and 600 μm, and preferably about 500 μm. The diameter of the circular voids may be included in a range extending from 1 mm to 1.5 mm, and preferably about 1.2 mm. In some embodiments, the second end 35 may include an array of linear voids (herein referred to as lines' or "trenches"). Each line may be aligned with the longitudinal axis of the waveguide 30 and may direct or assist in directing the attenuated portion of multiwavelength interrogating beam towards the detector 26.

In the illustrated embodiments, the cross-section of the probe head 24 is substantially circular, but one would readily understand that the shape of the cross-section may change, and may include other rounded shapes, such as and without being limitative, ellipse, bubble, globe, hemisphere, or rounded polygons. The shape of the probe head 24 could vary to include non-rounded shapes, e.g., parallelepiped, polygon, combinations and/or variants thereof, or any other shapes.

As illustrated in FIGS. 1 and 3, the light source 22 is positioned in the hollow chamber 31 such that it is substantially aligned with the first end 33. Alternatively, the light source 22 could be positioned elsewhere in the hollow chamber 31. In this embodiment, the optical probe 20 may include optical element(s) to shape, expand, collimate the multiwavelength interrogating beam or direct or guide the multiwavelength interrogation beam towards the first end 33 The light source 22 is preferably positioned with respect to the first cod 33 such that the first end 33 can receive the multiwavelength interrogating beam and inject the same into the waveguide 30, such that the multiwavelength interrogating beam can be guided in the waveguide 30.

As illustrated in FIGS. 1, 3, and 17A-B, the first end 33 may be coated with a first light-blocking layer 41 for optically shielding the first end 33 from the soil. The first light-blocking layer 41 may be provided on an outer surface 34 of the probe head 24, such that first light-blocking layer 41 covers at least a portion of the first end 33. The positioning of the first light-blocking layer 41 is with respect to the first end 33 is such that the multiwavelength interrogating beam does not propagate outside the waveguide 30 near or at the first end 33, but rather remains confined therein and guided towards the second end 35. In some embodiments, the first light-blocking layer 41 could also be reflective, in order to improve or facilitate guiding the multiwavelength interrogating beam in the waveguide 30. In some embodiments, the first light-blocking layer 41 could be opaque. The first light-blocking layer 41 can be made of any type of materials that does not or only minimally transmit light in the wavelengths included in the multiwavelength interrogating beam, such as for example an aluminum coating, a metal coating, an aluminum shoot and/or metal sheet.

Figure 17B:
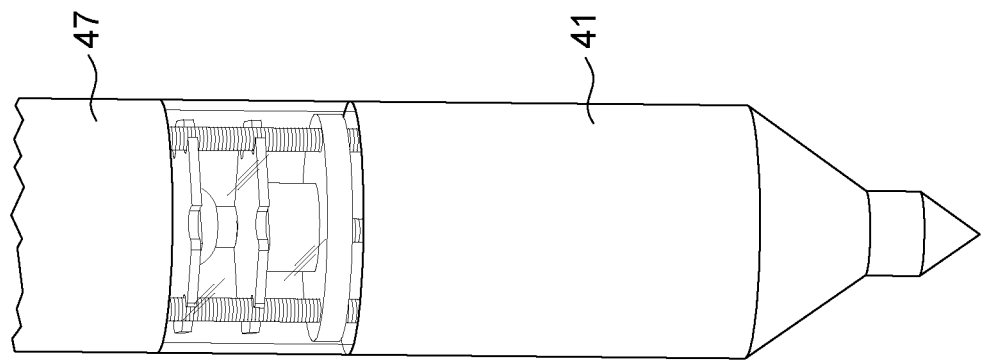
FIGS. 17A-B illustrate a first light-blocking layer positioned near a first end of a waveguide and a second light-blocking layer position near a second end of the waveguide.
Figure 17A:
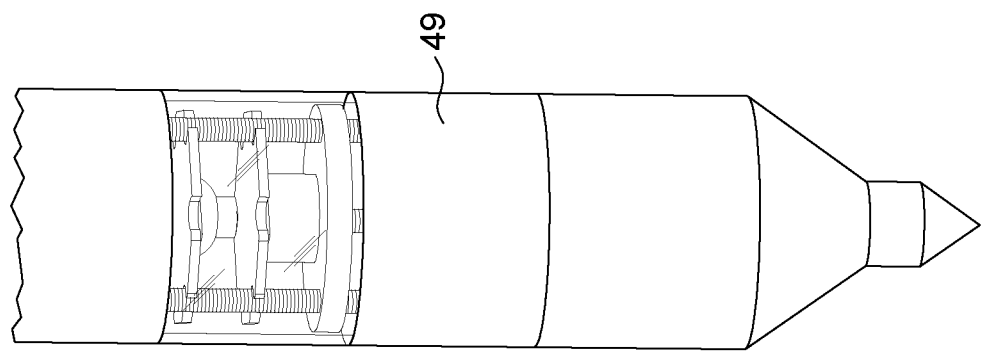

In some embodiments, such as the one illustrated in FIGS. 17A-B, the optical probe 20 may include a diffusive layer 49. The diffusive layer 49 can be provided between the first end 33 and the first-light blocking layer 41. The diffusive layer 49 can totally or partially cover an exterior surface of the first end 33. The diffusive layer 49 can be embodied, for example and without being limitative, by a reflective piece of material having a relatively low refractive index such as, for example and without being limitative, a white plastic (Teflon's) sheet or coating, a diffuse white paint or coating, and/or an unpolished of diffuse metal surface. The diffusive layer 49 can contribute to produce or generate a multimode (or diffuse) multiwavelength beam in the waveguide 30.

Referring to FIG. 2, the waveguide 30 also includes an interaction zone 37 located between the first end 33 and the second end 35. The interaction zone 37 is optically coupled with the soil when the probe head 24 is inserted in the underground area. The interaction zone 37 is configured to receive the multiwavelength interrogating beam from the first end 33. Upon reception of the multiwavelength interrogating beam, the first end 33 guides the beam into the waveguide 30 until the multiwavelength interrogating beam reaches the interaction zone 37. In the interaction zone 37, an evanescent portion of the multiwavelength interrogating beam propagates outside from the waveguide 30 and interacts with the soil. This results in the production of an attenuated portion of the multiwavelength interrogating beam in the waveguide 30. The attenuated portion of the multiwavelength interrogating beam is guided towards the second end 35. A schematic representation of the path followed by the multiwavelength interrogating beam, the evanescent portion of the multiwavelength interrogating beam and the attenuated portion of the multiwavelength interrogating beam is illustrated in FIGS. 2, 7, 8 and 13.

As illustrated in FIGS. 1, 2 and 17B, the optical probe 20 may include a second light-blocking layer 47. The second light-blocking layer 47 is provided on the outer surface 34 of the probe head 24, aligned or positioned near the second end 35, such that the attenuated portion of the multiwavelength interrogating beam does not propagate outside the waveguide 30 near the second end 35. The second light-blocking 47 may be similar to the first light-blocking layer 41 which has been previously described.

It has to be noted that, in some embodiments, the waveguide 30 is not a tubular transparent wall. In these embodiments, the probe head 24 could define an enclosure in which can be inserted or mounted the light source 22. The waveguide 30 could be a plate, a rod, fiber optic or the like. In these embodiments, the waveguide 30 can be a part or mounted to the probe head 24.

As previously mentioned, the waveguide 30 guides the multiwavelength interrogating beam from the first end 33 towards the second end 35, but it should be noted that the waveguide 30 is optically transparent to the spectral profile of the incoming multiwavelength interrogating beam (or at least a portion thereof) in the interaction zone 37, so that the evanescent portion of the multiwavelength interrogating beam can propagate outside from the waveguide 30.

In some embodiments, the waveguide 30 can be bubble-shaped in the interaction zone 37 to enhance or optimize the contact between the soil and the waveguide 30 in the interaction zone 37, as illustrated in FIGS. 9-12C. The bubble-shaped interaction zone 37 is generally larger than a remaining portion of the probe head 24. For example, a diameter of the bubble-shaped interaction zone 37 may be greater than a diameter of the waveguide 30 near the first end 33 and may be greater than a diameter of the waveguide 30 near the second end 33.

Figure 7:
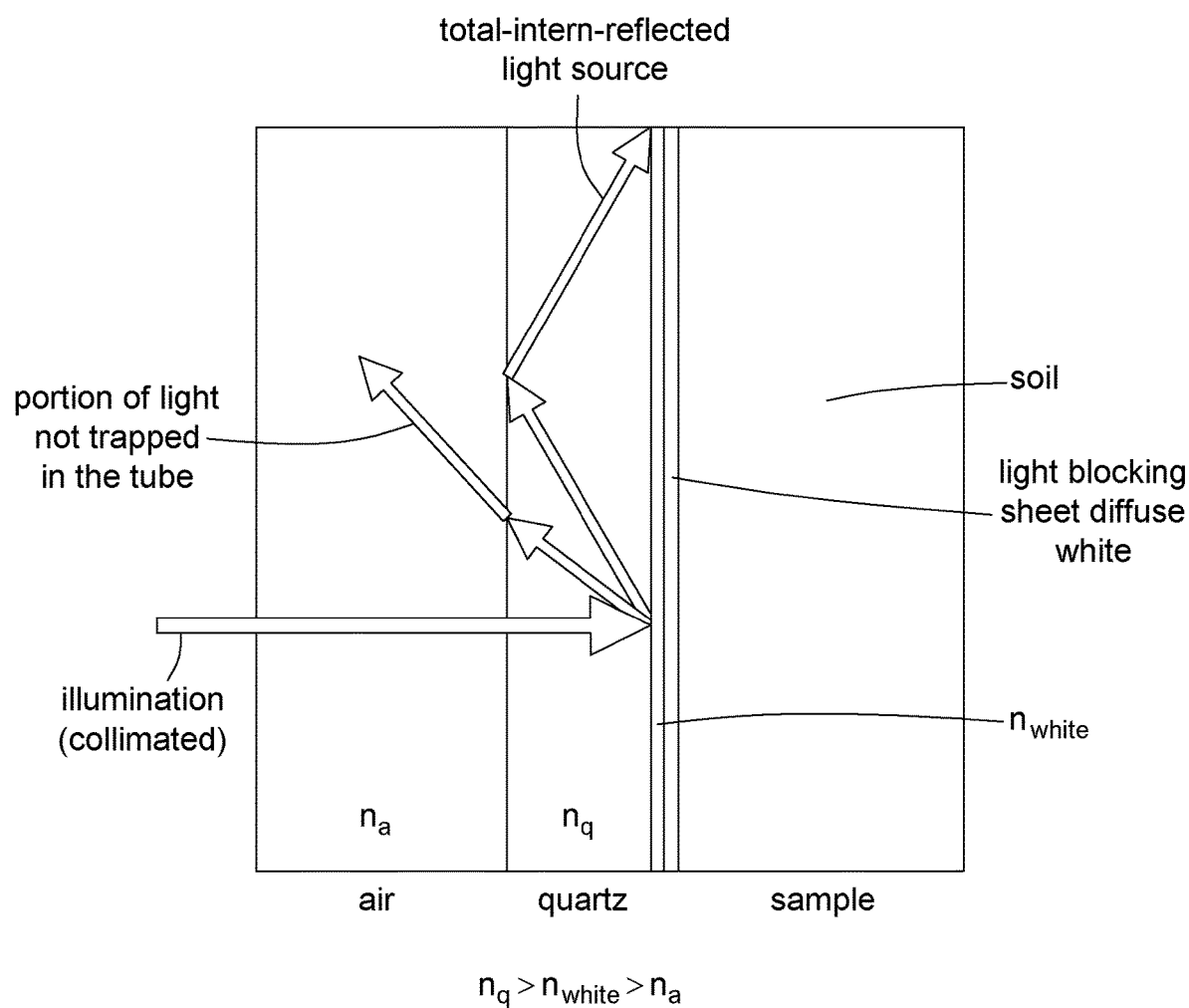
FIG. 7 is an enlarged view of the multiwavelength interrogating beam being injected and guided near a first end of a waveguide, in accordance with one embodiment.
Figure 8:
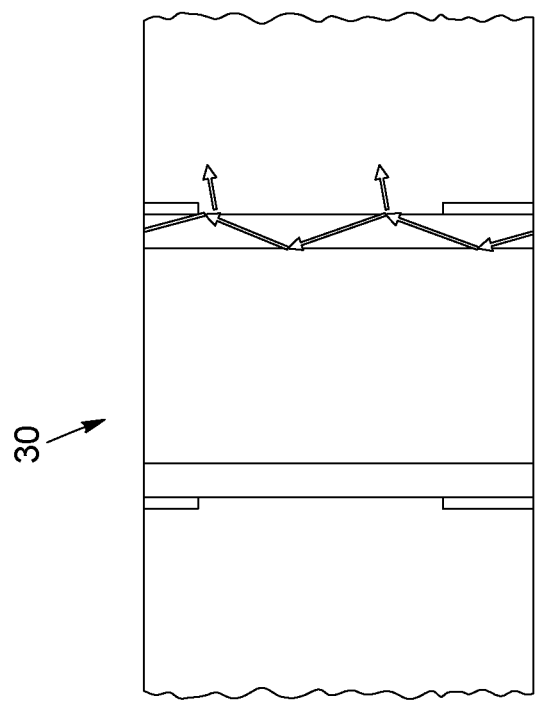
FIG. 8 illustrates an attenuation of the multiwavelength interrogating beam after its interaction with the soil.
Figure 10:
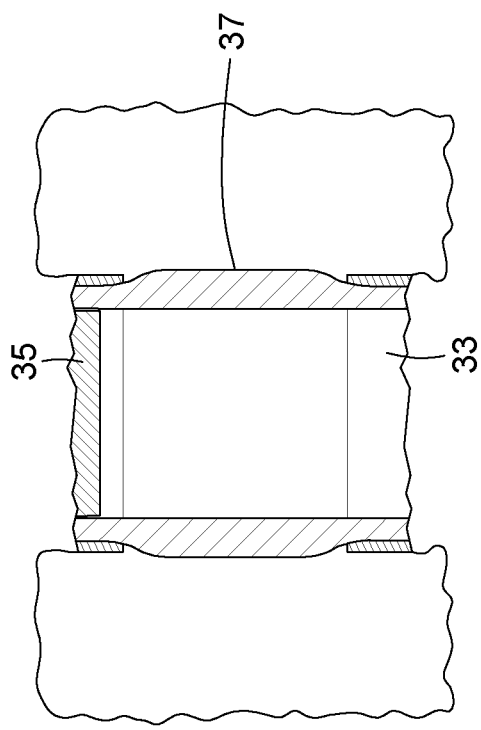
FIG. 10 is a cross-sectional view of FIG. 9.
Figure 9:
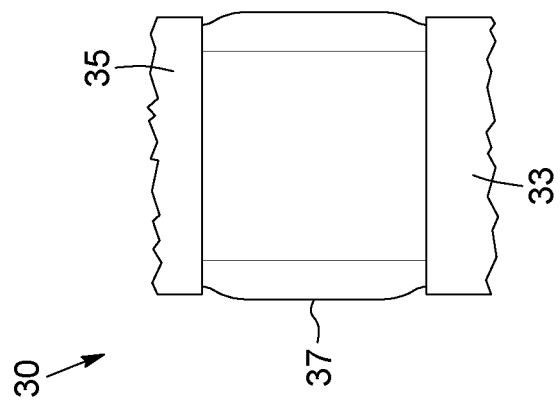
FIG. 9 is a side view of a waveguide having a bubble-shaped interaction zone.

The waveguide 30 is configured to collect the multiwavelength interrogating beam at the first end 33 and guides the same with total internal reflection, which is schematically illustrated in FIG. 7. Total internal reflection occurs when a propagating wave is incident onto the boundary between two media at an angle larger than a critical angle with respect to the normal to the surface. The two media could, for example, and without being limitative, the waveguide 30 and the first light-blocking layer 41, the waveguide 30 and the diffusive layer 49, the waveguide 30 and the gas contained in the probe head 24, the waveguide 30 and the second light-blocking layer 47, or the waveguide 30 and the soil (in the interaction zone 37). The critical angle is the angle of incidence above which the total internal reflection occurs, i.e., the angle above which the resulting light will be guided in the waveguide 30. The critical angle $\theta_c$ is given by Snell's law and can be written as:

$$\theta_c = \arcsin\left(\frac{n_2}{n_1}\right) \quad (1)$$

wherein $n_2$ is the refractive index of the second medium and $n_1$ is the refractive index of the first media.

The probe head 24 and the waveguide 30 may be made from a material impermeable to the soil solution present in the soil, i.e., the soil solution cannot diffuse or circulate within the hollow chamber 31 and so does not penetrate the probe head 24. As such, the probe head 24 and the waveguide 30 are generally made from a non-porous material, or the porosity of the material is such that the soil solution stays outside of the probe head 24 and the waveguide 30. A broad variety of materials could be used for the waveguide 30, for example and without being limitative: clear fused quartz, quartz, sapphire, other types of glass and acrylic. Broadly, any optical materials configured for guiding light can be included in the waveguide 30.

As for its positioning, the probe head 24, and in some instances, the waveguide 30, are typically fixed near or at the extremity of the bottom end portion 53 of the tube 39 forming the casing 46. More particularly, if the extremity of the bottom end portion 53 of the tube 39 is open (i.e., provided with a hole) a portion of the waveguide 30 can be slidably inserted and engaged therein (i.e., in the open extremity of the bottom end portion 53 of the tube 39). It is to be rioted that supplementary fixing components or devices could be used to maintain the waveguide 30 secured to the extremity of the bottom end portion 53 of the tube 39, such as buttons, snaps, screws, glue, tape, welding, slits, guiding rails, combinations thereof, or any other components and/or means which would allow the waveguide 30 to be affixed to the tube 39.

In other embodiments, the bottom end portion 53 of the tube 39 and/or a region near its extremity could be threaded in its inner portion, and, similarly, a portion of the waveguide 30 or a piece mounted near the first end 33 of the waveguide 30 could also be threaded on its outer portion, such that the waveguide 30 or the piece mounted near the first end 33 of the waveguide 30 could be screwed (i.e., secured after a rotation) to the extremity of the bottom end portion 53 of the tube 39.

Referring to FIGS. 1, 11A-B, 14, 15C and 16A-C, the optical probe 20 includes an optical element 29 mounted in the hollow chamber 31, near or at the second end 35 of the waveguide 30. The optical element 29 is configured to guide the attenuated portion of the multiwavelength interrogating beam guided in the waveguide 30 from the waveguide 30 to the detector 26. In some embodiments, the optical element 29 is positioned near or aligned with the second end 35. In some embodiments, the optical element 29 is optically coupled with the waveguide 30 for scattering the attenuated portion of the multiwavelength interrogating beam inside the probe head 24.

In some embodiments, the optical element 29 is cone shaped. In some embodiments, the optical element 29 conforms with the inner surface 32 of the probe head 24. In some embodiments, the optical element 29 has a bottom portion, and the second end 35 has a top portion and the bottom portion of the optical element 29 abuts the top portion of the second end 35. The mechanical contact between the bottom portion of the optical element 29 and the second end 35 of the waveguide 30 allows optically coupling the waveguide 30 and the optical element 29. In some embodiments, the optical element 29 is made from silicone.

In some embodiments, the optical element 29 may be a transparent optical guide, extending from the second end 35 of the waveguide 30 to the detector. In some embodiments, the optical probe 20 further comprises an optical fiber 45 positioned between the optical element 29 and the detector 26, as illustrated for example in FIGS. 1, 11B, 12B, 14 and 15C. The optical fiber 45 is configured to optically couple the detector 26 with the optical element 29.

Figure 11A:
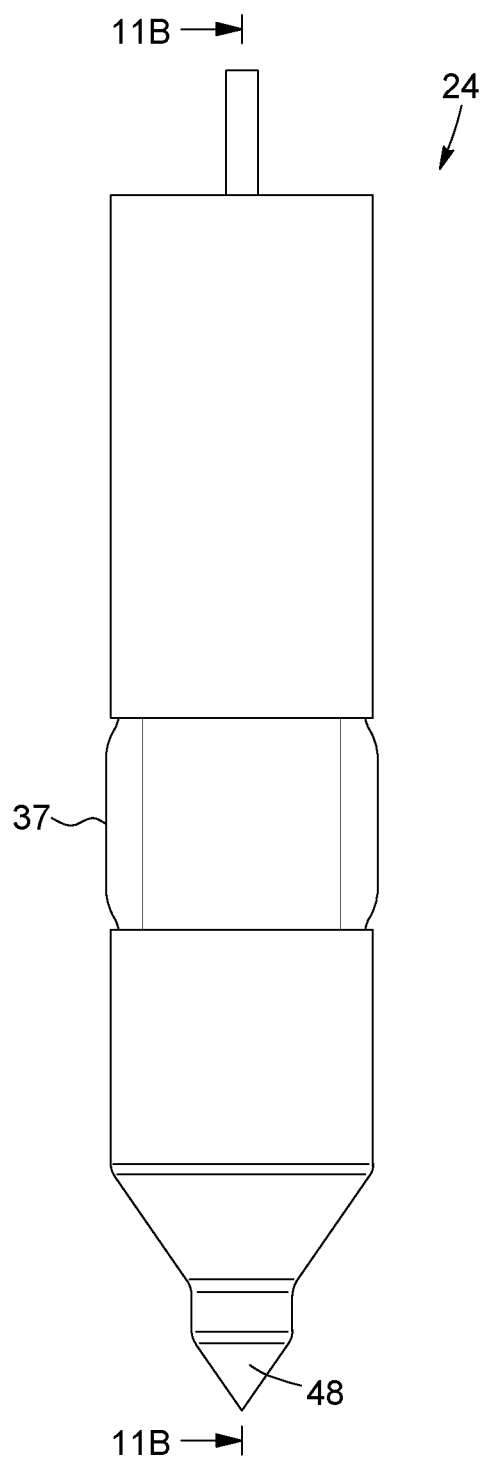
FIGS. 11A-B illustrate an optical element integral 4 formed with a second end of a waveguide, in accordance with one embodiment.
Figure 11B:
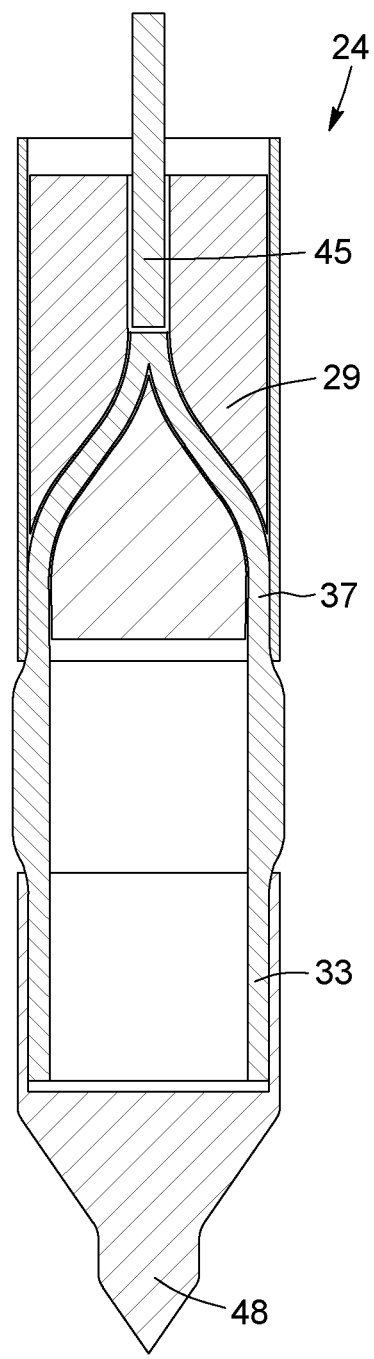
Figure 13:
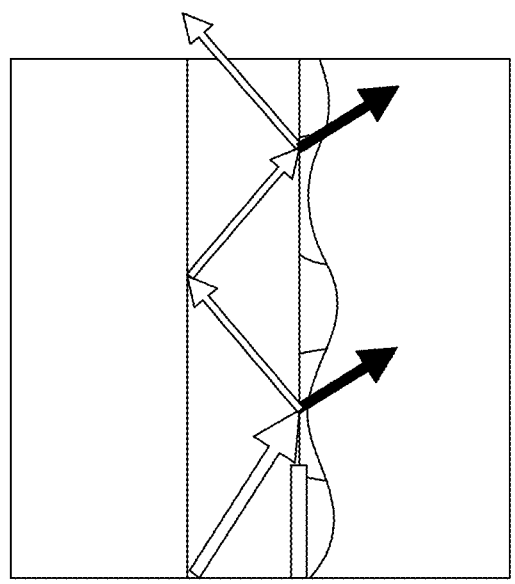
FIG. 13 illustrates an interaction between a multiwavelength interrogating beam and the soil.
Figure 14:
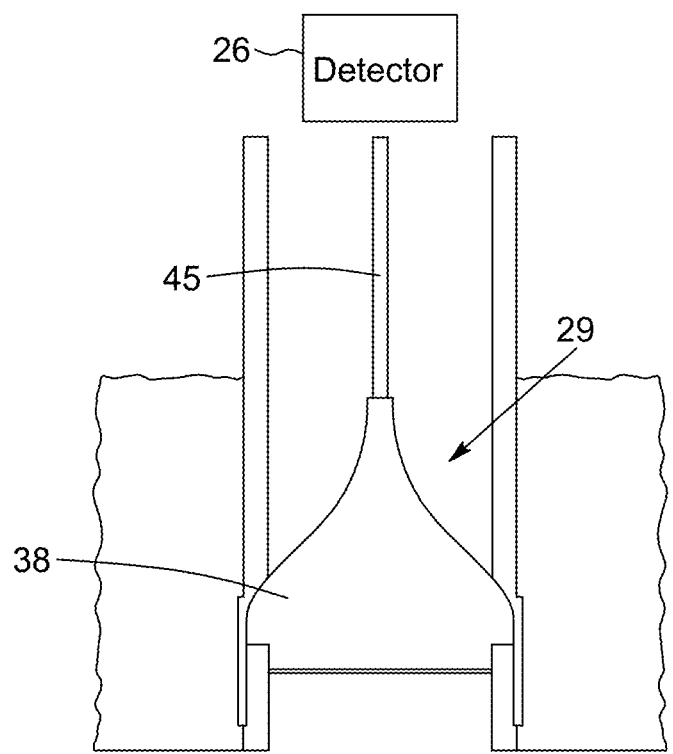
FIG. 14 shows a cone-shaped optical element contacting a second cud of a waveguide, in accordance with one embodiment.

In some embodiments, such as the one illustrated in FIGS. 11A-B, the optical probe includes an optical element 29 integrally formed with the second end 35 of the waveguide 30. The optical element 29 is configured to guide the attenuated portion of the multiwavelength interrogating beam from the second end 35 of the waveguide 30 towards the detector 26. In some embodiments, the optical element 29 is cone shaped. In some embodiments, the optical element 29 has a bottom portion, and the second end 35 has a top portion. The bottom portion of the optical element 29 is aligned with the top portion of the second end 35. In some embodiments, the optical probe 20 further comprises an optical fiber 45 positioned between the optical element 29 and the detector 26. The optical fiber 45 is configured to optically couple the detector 26 with the optical element 29.

In some embodiments, the optical element 29 may be a diffusing surface, a coating of paint, or any other diffusing material applicable to a glass material.

In some embodiments, the optical element 29 may be made from an optically clear epoxy or a resin matrix having air bubbles therein. Such an optical material could be in contact the inner surface 32 of the probe head 24.

In some embodiments, the optical probe 20 further comprises at least one optical fiber (not illustrated) for guiding the attenuated portion of the multiwavelength interrogating beam from the waveguide 30 towards the detector 26. The optical fiber can be in mechanical contact with the waveguide 30 or a portion thereof. In such embodiments, the waveguide 30 can be provided with at least one hole for receiving the optical fiber therein. Such a hole can be provided near or at the second end 35. More particularly, the bole could be provided in a solid portion of the waveguide 30 and extends in a direction parallel to a longitudinal axis of the waveguide 30, i.e., such that the input of the optical fiber is aligned within the longitudinal axis of the waveguide 30 (i.e., the propagation direction). The hole can be deep enough that the optical fiber could be inserted and maintained in place with or without affixing means. This configuration allows the optical fiber to collect the attenuated multiwavelength interrogating beam. Typically, each hole is sized and configured to receive one optical fiber. It is to be noted that the optical fiber(s) could also be attached to the transparent wall 30 using appropriate fixing and/or sticking means.

In some embodiments, an additional layer made of, for example and without being limitative, a silver-based material, aluminum, or any other reflective coating(s) may be provided on the inner surface 32 and/or the outer surface 34 of the probe head 24. In some embodiments, the use of such a reflective coating could increase the signal produced by the detector 26. Indeed, if the transfer of light is more efficient, as it could be the case when an additional layer made of a reflective coating is provided, the detector 26 can receive more light, and therefore produces a stronger signal.

It is to be noted that the light source 22, the probe head 24 and/or the detector 26 could be coupled to other optical components (not shown) configured to alter at least some of the properties of the light prior or after its interaction with the soil under investigation. The expression "optical components" herein refers, but is not limited to lenses, mirrors, filters, and other suitable reflective, refractive and/or diffractive optical components. It is to be noted that the relative position of the light source 22, the probe head 24 and/or the detector 26 may also be adjustable.

In some embodiments, such as the one illustrated in FIGS. 3 and 6, the optical probe 20 may include a sensing tip 48 provided near or at an extremity of the probe bead 24. The sensing tip 48 can be configured to measure at least one of the properties of the soil, such as for example and without being limitative, the electroconductivity, the pH of the soil and/or any other properties which can be sensed with the sensing tip 48.

In some embodiments, the bottom extremity (or "distal end") of the optical probe 20 is tapered (i.e., the end of the probe head 24 may reduce in diameter or thickness towards an extremity of end of the probe head 24). The bottom extremity of the optical probe 20 is typically configured, sized and positioned to allow the optical probe 20 to be inserted to the ground upon application of a force. In some embodiments, the optical probe 20 may include a helicoidal end part configured to enter the ground when being pushed towards the ground and rotated about a rotation axis, so that the probe head 24 is exposed to the soil in the underground area. In such embodiments, the helicoidal end part has a dimension and mechanical properties which allow sufficient engagement of the optical probe 20 with the ground, thus providing stability to the optical probe 20, when inserted into the soil. In some embodiments, the optical probe 20 can be inserted at two different depths, e.g., about 15 cm and about 30 cm. Of course, one would have readily understood that the optical probe 20 can be inserted at any depth in the field. For example, and without being limitative, the probe head 24 can be inserted at a depth ranging from about 0 cm to about 80 cm under the soil surface.

In some embodiments, the bottom extremity of the optical probe 20 may be made from a material that is different from the material(s) forming the probe head 24. By way of an example, the extremity of the optical probe 20 could be made from epoxy resin, acrylonitrile butadiene styrene (ABS) plastic, polylactic acid (PLA) plastic, aluminum or any other suitable materials.

Referring back to FIG. 1, the detector 26 is optically coupled with the waveguide 30 and may be positioned near or aligned with the second end 35. The detector 26 is configured to receive the attenuated portion of the multiwavelength interrogating beam and output a detector signal. Generally, the detector 26 is positioned and configured to receive the attenuated portion of the multiwavelength interrogating beam being guided in the waveguide 30 after the interaction of the evanescent portion of the multiwavelength interrogating beam with the soil or media in contact with the probe head.

In some embodiments, the detector 26 may be a light detector. An example of a light detector could be, but is not limited to a spectrometer, i.e., a device to measure the spectral properties of the attenuated portion of the multiwavelength interrogating beam. The detector 26 is generally responsive in the region of operation of the light source 22 or at least a portion thereof. The detector 26 is sensitive to at least a portion of the wavelengths included in the spectral profile of the light source 22 or LEDs 28. It will be readily understood that more than one light detector could be used, in order to cover the whole spectral content of the attenuated portion of the multiwavelength interrogating beam. Once received by the detector 26, the attenuated portion of the multiwavelength interrogating beam may be converted to an electrical signal, electrical data and/or any other type of data using techniques already known by one skilled in the art. In some embodiments, the processor 50 is an external computer. The external computer can be operatively connected to the optical probe 20, either wirelessly or through physical connection, and can be configured for performing at least one of the following operations: sending instructions to the optical probe 20 or one of its components (e.g., the light source 22 or the detector 26), receiving data from the optical probe 20, controlling different parameters of the optical probe 20, treating the collected data and/or generating visual representations (e.g., graph) of the soil conditions. The term "computer" (or "computing device") is used to encompass computers, servers and/or specialized electronic devices which receive, process and/or transmit data. Computers are generally part of "systems" and include processing means, such as microcontrollers and/or microprocessors, CPUs or are implemented on FPGAs, as examples only. The processing means are used in combination with storage medium, also referred to as "memory" or "storage means". Storage medium can store instructions, algorithms, rules and/or data to be processed. Storage medium encompasses volatile or non-volatile/persistent memory, such as registers, cache, RAM, flash memory, ROM, as examples only. The type of memory is, of course, chosen according to the desired use, whether it should retain instructions, or temporarily store, retain or update data. One skilled in the art will therefore understand that each such computer typically includes a processor (or multiple processors) that executes program instructions stored in the memory or other non-transitory computer-readable storage medium or device (e.g., solid state storage devices, disk drives, etc.). The various functions, modules, services, units or the like disclosed hereinbelow can be embodied in such program instructions, and/or can be implemented in application-specific circuitry (e.g., ASICs or FPGAs) of the computers. Where a computer system includes multiple computers these devices can, but need not, be co-located. In some embodiments, a computer system can be a cloud-based computing system whose processing resources are shared by multiple distinct business entities or other users.

Figure 18A:
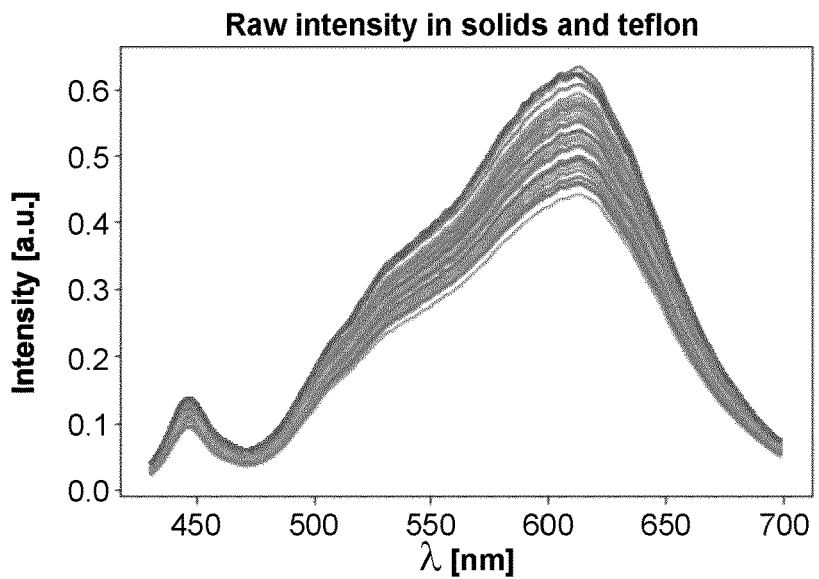
FIGS. 18A-C illustrate the determination of the spectral content of the evanescent portion of the multiwavelength interrogating beam.
Figure 18B:
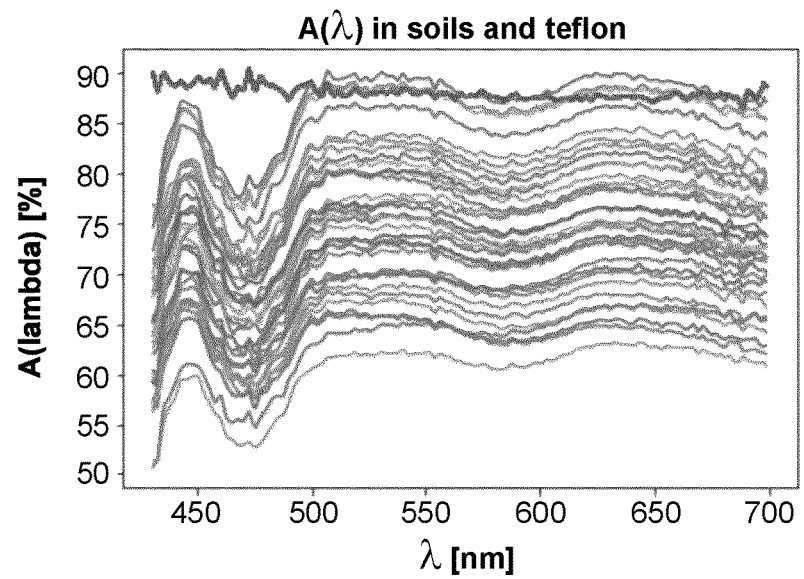
Figure 18C:
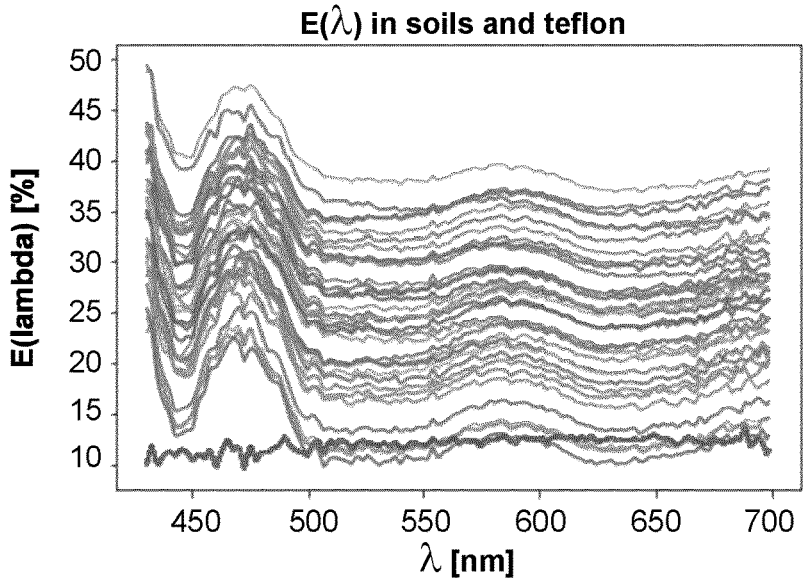

As illustrated in FIG. 15C, the processor 50 is operatively connected to the detector 26 and is configured to receive the detector signal and determine a spectral content of the evanescent portion of the multiwavelength interrogating beam based on the multiwavelength interrogating beam and the attenuated portion of the multiwavelength interrogating beam. The spectral content is representative of at least one characteristic of the soil. As previously mentioned, the characteristics of the soil are globally referred as the soil condition, and could include many different properties, such as the ones which have been previously described. Based on the knowledge or pre-characterization of the optical properties (including the spectral content) of the multiwavelength interrogating beam as generated and the detection of spectral properties of the attenuated portion of the multiwavelength interrogating beam, the step of determining the spectral content of the evanescent portion can be achieved by spectrally subtracting the attenuated portion of the multiwavelength interrogating beam from the original multiwavelength interrogating beam, as illustrated in FIGS. 18A-C.

As it will be readily understood, the processor 50 can be implemented as a single unit or as a plurality of interconnected processing sub-units. Also, the processor can be embodied by a computer, a microprocessor, a microcontroller, a central processing unit, or by any other type of processing resource or any combination of such processing resources configured to operate collectively as a processor. The processor 50 can be implemented in hardware, software, firmware, or any combination thereof, and be connected to the various components of the spectral identification system via appropriate communication ports.

Figure 19A:
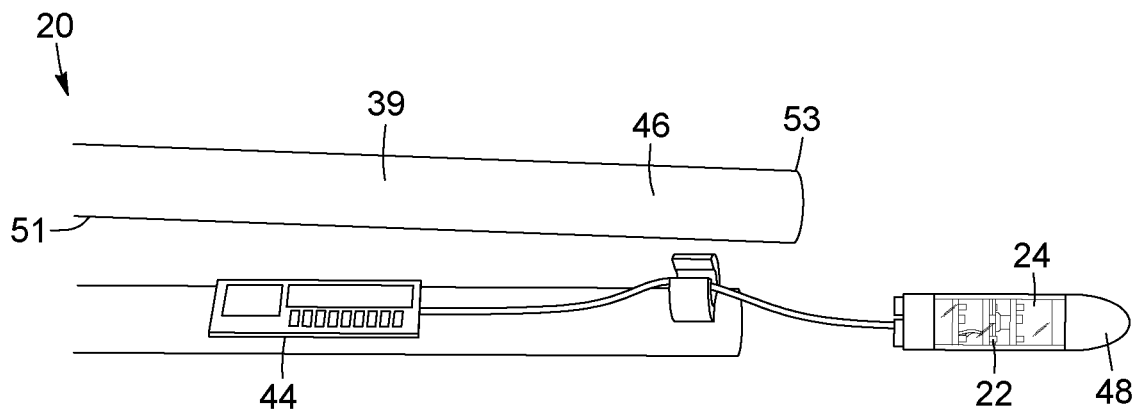
FIGS. 19A-B show a probe head being assembled to remaining portions of the optical probe, in accordance with one embodiment.

Referring to FIG. 19A, the optical probe 20 can be provided with an electrical circuit 44 for powering the light source 22 and the detector 26. The design and configuration of the electrical circuit 44 may vary according to the targeted application, but could include appropriate electronics components, such as for example and without being limitative resistors, switches, amplifiers, filters, diodes, transistor, and/or any other components already known by one skilled in the art.

The optical probe 20 may also include a control unit for operating and controlling at least one of the light source 22 and the detector 26, for example and without being limitative, through the electrical circuit 44. The control unit can be connected or part of the processor 50. Alternatively, the control unit of the optical probe 20 could also be operatively connectable to a computer, a smartphone, or any other type of devices or portable devices.

In some embodiments, the optical probe 20 may include a power unit for powering the electrical circuit 44. For example, and without being limitative, the power unit could include at least one battery. In some embodiments, the battery has a cycle life of about 1500 measurements. These embodiments can be useful when the optical probe 20 is used in remote locations and can also provide the optical probe 20 with a certain degree of autonomy.

Figure 19B:
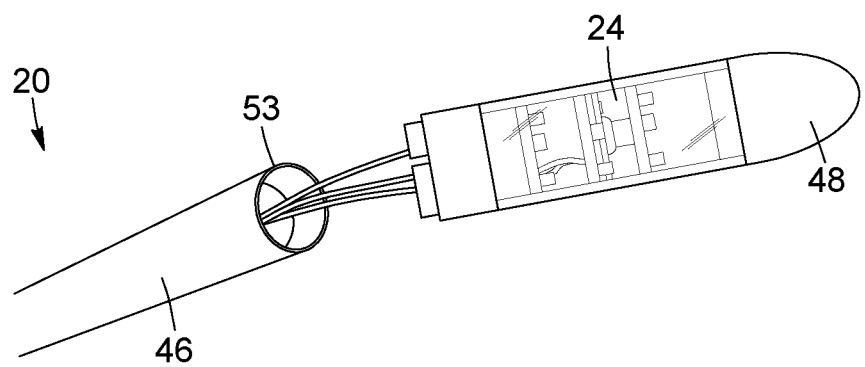

Referring to FIG. 19A-B, the optical probe 20 may include a casing 46. The casing 46 may include a tube 39. The tube 39 typically has two end portions a top end portion 51 and a bottom end portion 53. The top end portion 51 may be provided with handles, or similar structure, near or at its extremity, to help the user inserting the optical probe 20 into the ground or removing the optical probe 20 from the ground. The top end portion 51 usually refers to the portion of the tube 39 (or the casing 46) being exposed to ambient air when the optical probe 20 is inserted in the ground for analysis, while the bottom end portion 53 usually refers to the portion of the tube 39 (or the casing 46) being exposed to the underground area. The probe head 24, and more particularly the waveguide 30, is typically mounted and/or affixed to the bottom end portion of the tube 39. Other details regarding the casing 46 will be provided later.

The casing 46 is sized and configured to receive the electrical circuit 44 therein. In some embodiments, the casing 46 has a hollow portion or is at least partially hollow and houses the electrical circuit 44. The probe head 24 can also be mounted to the bottom end portion 53 of the casing 46, i.e., the extremity that is the closest to the ground (in comparison with the top end portion 51). As it has been previously described, at least a portion of the probe head 24 can be engaged with or mounted to the casing 46.

In some embodiments, the casing 46 has a height ranging from about 30 cm to about 100 cm and the probe head 24 has a height ranging from about 0.5 cm to about 5 cm. In such embodiments, the optical probe 20 has a total height of about 35 cm. In some embodiments, the height of the casing 46 can be adjustable, e.g., the height of the casing can be retractable.

The casing 46 may be made from a broad variety of material. For example, and without being limitative, the casing 46 may be made from any solid material such as polymers, including but not limited to limitative vinyl, fiberglass and rigid polyvinyl chloride (PVC), metals and metal alloys, including but not limited to aluminum and aluminium alloys, stainless steel, brass, copper, combinations thereof, or any other material that can be used to house and, in some instances, protect the circuits 44 and to which the probe head 24 can be mounted through appropriate attachment(s). Of course, the casing 46 can have various geometrical configurations (i.e., size and dimensions). As depicted however, the casing 46 has a cylindrical shape. i.e., the casing 46 is tubular. It will be readily understood that the casing 46 could alternatively have a completely different shape. It has to be noted that the various examples provided herein are not limitative and serve an illustrative purpose only.

In accordance with another broad aspect, there is provided an optical probe 20 for analysing a soil located in an underground area. The optical probe 20 includes a probe head 24 insertable into the underground area to contact the soil. The probe head 24 includes a waveguide 30 having opposite first and second ends 33, 35, both optically shielded from the soil. The optical probe 20 includes a light source 22 configured to generate a multiwavelength interrogating beam and optically coupled to the first end 33 of the waveguide 30 so that the multiwavelength interrogation beam is inputted in the waveguide 30 to propagate towards the second end 35. The optical probe 20 includes a detector 26 optically coupled to the second end 35 of the waveguide 30 to detect said multiwavelength interrogation beam. The waveguide 30 includes an unshielded interaction zone 37 extending between the first and second ends 33,35 providing a wavelength-dependent attenuation of the multiwavelength interrogation beam through interaction with the soil. In some embodiments, the optical probe 20 includes a processor 50. The processor 50 is configured to receive a detector signal from the detector 26 and evaluate therefrom the wavelength-dependent attenuation of the multiwavelength interrogation beam. The wavelength-dependent attenuation of the multiwavelength interrogation beam is representative of at least one characteristic of the soil. Of note, the optical probe 20 is compatible with the embodiments of the technology having been previously described.

Method

In accordance with another aspect, there is provided a method for analysing a soil located in an underground area. The method includes inserting a probe head in the underground area to contact the soil, the probe head including a waveguide, the waveguide including a first end, a second end opposite the first end and an interaction zone located between the first end and the second end; projecting a multiwavelength interrogating beam towards the first end; guiding, in the waveguide, the multiwavelength interrogating beam, an evanescent portion of the multiwavelength interrogating beam propagating outside from the waveguide and interacting with the soil in the interaction zone, thereby producing an attenuated portion of the multiwavelength interrogating beam in the waveguide, the attenuated portion of the multiwavelength interrogating beam being guided towards the second end; detecting the attenuated portion of the multiwavelength interrogating beam; and determining a spectral content of the evanescent portion of the multiwavelength interrogating beam based on the multiwavelength interrogating beam and the attenuated portion of the multiwavelength interrogating beam, the spectral content being representative of at least one characteristic of the soil.

In some embodiments, the attenuated multiwavelength interrogation beam propagates from the first end towards the second end by total internal reflection by total internal reflection.

In some embodiments, the characteristics of the soil are selected from the group consisting of level of nutrients, level of available nutrients, ionic concentration of the soil solution, temperature, moisture, pH, level of organic matter and soil texture. Of note, any other properties of the soil that may be determined based on the spectral content of the evanescent portion of the multiwavelength interrogating beam, the multiwavelength interrogating beam and the attenuated portion of the multiwavelength interrogating beam could also be investigated using the present techniques.

In some embodiments, the method further includes measuring at least one of an electroconductivity and a pH of the soil with a sensing tip mounted near or at an extremity of the probe head.

In some embodiments, determining the spectral content of the evanescent portion of the multiwavelength interrogating beam includes producing an output signal representative of the at least one characteristic of the soil and processing the output signal.

In some embodiments, inserting the probe head in the underground area to contact the soil includes inserting the probe head at a depth ranging from about 0 cm to about 80 cm under the soil surface.

Several alternative embodiments and examples have been described and illustrated herein. The embodiments described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. The present examples and embodiments, therefore, are to be considered in all respects as illustrative and not restrictive. Accordingly, while specific embodiments have been illustrated and described, numerous modifications come to mind without significantly departing from the scope defined in the appended claims.

What is claimed is:

1. An optical probe for analysing a soil located in an underground area, the optical probe comprising:
   a light source configured to generate a multiwavelength interrogating beam;
   a probe head insertable into the underground area to contact the soil, the probe head comprising a waveguide, the waveguide comprising:
     a first end optically shielded from the soil and optically coupled with the light source, the first end being configured to receive the multiwavelength interrogating beam, the multiwavelength interrogating beam being guided in the waveguide;
     a second end optically shielded from the soil, the second end being opposite the first end; and
     an interaction zone located between the first end and the second end, the interaction zone being optically coupled with the soil when the probe head is inserted in the underground area and being configured to receive the multiwavelength interrogating beam from the first end, an evanescent portion of the multiwavelength interrogating beam propagating outside from the waveguide and interacting with the soil, thereby leaving an attenuated portion of the multiwavelength interrogating beam in the waveguide, the attenuated portion of the multiwavelength interrogating beam being guided towards the second end;
   a detector optically coupled with the waveguide near or at the second end, the detector being configured to receive the attenuated portion of the multiwavelength interrogating beam and output a detector signal; and
   a processor configured to receive the detector signal and determine a spectral content of the evanescent portion of the multiwavelength interrogating beam based on the multiwavelength interrogating beam and the attenuated portion of the multiwavelength interrogating beam, the spectral content being representative of at least one characteristic of the soil.

2. The optical probe of claim 1, wherein the attenuated portion of the multiwavelength interrogating beam propagates from the first end towards the second end by a total internal reflection.

3. The optical probe of claim 1, wherein the waveguide has a multimode structure configured to guide therein a multimode multiwavelength interrogating beam.

4. The optical probe of claim 1, wherein the light source comprises a stack of light-emitting diodes (LEDs), the stack of LEDs comprising:
   a first LED having a first spectral profile comprising a first waveband centered around 550 nm; and
   a second LED having a second spectral profile comprising a second waveband centered around 700 nm.

5. The optical probe of claim 1, wherein the waveguide defines a hollow chamber within the probe head, the hollow chamber being filled with air or nitrogen.

6. The optical probe of claim 1, wherein the waveguide includes at least one transparent wall.

7. The optical probe of claim 1, wherein the first end has an outer surface, the outer surface of the first end being coated with a first light-blocking layer, and the second end has an outer surface, the outer surface of the second end being coated with a second light-blocking layer.

8. The optical probe of claim 1, wherein the first end comprises a first optical structure, the first optical structure being configured to confine and guide the multiwavelength interrogating beam within the first end of the waveguide, the first optical structure comprising a periodic pattern, the period pattern comprising a plurality of lines, an array of points or a grating.

9. The optical probe of claim 1, wherein the second end comprises a second optical structure, the second optical structure being configured to direct the attenuated portion of the multiwavelength interrogating beam towards the detector, the second optical structure comprising a periodic pattern, the periodic pattern comprising a plurality of lines, an array of points or a grating.

10. The optical probe of claim 1, wherein the waveguide is bubble-shaped in the interaction zone.

11. The optical probe of claim 1, further comprising an optical element mounted in the probe head and aligned with the second end of the waveguide, the optical element being optically coupled with the second end of the waveguide and being configured to guide the attenuated portion of the multiwavelength interrogating beam from the second end of the waveguide towards the detector.

12. The optical probe of claim 1, further comprising an optical element, wherein the optical element is integrally formed with the second end of the waveguide, the optical element being configured to guide the attenuated portion of the multiwavelength interrogating beam from the second end of the waveguide towards the detector.

13. The optical probe of claim 1, wherein the at least one characteristic of the soil is selected from the group consisting of: a level of nutrients, a level of available nutrients, an ionic concentration of a soil solution, a temperature, a moisture, pH, and a level of organic matter and soil texture.

14. A method for analysing a soil located in an underground area, the method comprising steps of:
- inserting a probe head in the underground area to contact the soil, the probe head comprising a waveguide, the waveguide comprising a first end, a second end opposite the first end, and an interaction zone located between the first end and the second end;
- projecting a multiwavelength interrogating beam towards the first end;
- guiding, in the waveguide, the multiwavelength interrogating beam, an evanescent portion of the multiwavelength interrogating beam propagating outside from the waveguide and interacting with the soil in the interaction zone, thereby producing an attenuated portion of the multiwavelength interrogating beam in the waveguide, the attenuated portion of the multiwavelength interrogating beam being guided towards the second end;
- detecting the attenuated portion of the multiwavelength interrogating beam; and
- determining a spectral content of the evanescent portion of the multiwavelength interrogating beam based on the multiwavelength interrogating beam and the attenuated portion of the multiwavelength interrogating beam, the spectral content being representative of at least one characteristic of the soil.

15. The method of claim 14, wherein the attenuated portion of the multiwavelength interrogating beam propagates from the first end towards the second end by a total internal reflection.

16. The method of claim 14, wherein the at least one characteristic of the soil is selected from the group consisting of: a level of nutrients, a level of available nutrients, an ionic concentration of a soil solution, a temperature, a moisture, pH, a level of organic matter and soil texture.

17. The method of claim 14, wherein the determining the spectral content of the evanescent portion of the multiwavelength interrogating beam comprises producing an output signal representative of the at least one characteristic of the soil, and processing the output signal.

18. The method of claim 14, wherein the inserting the probe head in the underground area to contact the soil comprises inserting the probe head at a depth ranging from about 0 cm to about 80 cm under a soil surface.

19. An optical probe for analysing a soil located in an underground area, the optical probe comprising:
- a probe head insertable into the underground area to contact the soil, the probe head comprising a waveguide having opposite a first end and a second end, both of which are optically shielded from the soil;
- a light source configured to generate a multiwavelength interrogating beam and optically coupled to the first end of the waveguide so that the multiwavelength interrogating beam is inputted in the waveguide to propagate towards the second end; and
- a detector optically coupled to the second end of the waveguide to detect the multiwavelength interrogating beam;

wherein the waveguide comprises an unshielded interaction zone extending between the first end and the second end providing a wavelength-dependent attenuation of the multiwavelength interrogating beam through an interaction with the soil.

20. The optical probe according to claim 19, further comprising a processor receiving a detector signal from the detector and configured to evaluate therefrom the wavelength-dependent attenuation of the multiwavelength interrogating beam, the wavelength-dependent attenuation of the multiwavelength interrogating beam being representative of at least one characteristic of the soil.

* * * * *